US008808165B2

(12) United States Patent
Okabe

(10) Patent No.: US 8,808,165 B2
(45) Date of Patent: Aug. 19, 2014

(54) CASING OF CAPSULE ENDOSCOPE, CAPSULE ENDOSCOPE KIT, ASSEMBLY METHOD OF CAPSULE ENDOSCOPE KIT AND ASSEMBLY DEVICE OF CAPSULE ENDOSCOPE KIT

(71) Applicant: Olympus Medical Systems Corp., Tokyo (JP)

(72) Inventor: Kentaro Okabe, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/670,959

(22) Filed: Nov. 7, 2012

(65) Prior Publication Data
US 2013/0102844 A1 Apr. 25, 2013

Related U.S. Application Data

(63) Continuation of application No. PCT/JP2012/061906, filed on May 9, 2012.

(30) Foreign Application Priority Data

May 13, 2011 (JP) ................................. 2011-108796

(51) Int. Cl.
*A61B 1/00* (2006.01)
*A61B 1/04* (2006.01)

(52) U.S. Cl.
CPC ............... *A61B 1/00* (2013.01); *A61B 1/00142* (2013.01); *A61B 1/00144* (2013.01)
USPC ............ 600/122; 600/109; 600/121; 600/133

(58) Field of Classification Search
CPC .. A61B 1/041; A61B 1/00057; A61B 1/0011; A61B 1/00142; A61B 1/00144; A61B 1/00147; A61B 1/01; A61B 1/051; A61B 1/053; A61B 1/055; A61B 5/6861; A61B 2562/162
USPC .......... 600/109, 102, 112, 119, 121–123, 133
See application file for complete search history.

(56) References Cited

U.S. PATENT DOCUMENTS

| 7,775,971 | B2 * | 8/2010 | Fujimori et al. | ............... 600/110 |
| 7,998,059 | B2 * | 8/2011 | Fujimori | ....................... 600/109 |

(Continued)

FOREIGN PATENT DOCUMENTS

| CN | 101098652 A | 1/2008 |
| JP | 2006-87524 A | 4/2006 |

(Continued)

OTHER PUBLICATIONS

International Search report PCT/JP2012/061906 dated Aug. 7, 2012.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An inner casing according to the present invention includes a hole which is a holding portion that is provided at the center of a base portion having a planar shape so as to protrude in a direction orthogonal to a principal surface of the base portion and hold a capsule endoscope and a plurality of step portions each protruding from a side surface of the hole and abutting on an area of an outer surface of a hemispheric dome portion, which is located inside an optical viewing angle of the capsule endoscope and which does not contribute to generation of an image captured by the capsule endoscope to realize alignment in a longitudinal direction of the capsule endoscope.

28 Claims, 28 Drawing Sheets

(56) References Cited

U.S. PATENT DOCUMENTS

| | | | |
|---|---|---|---|
| 8,128,560 B2* | 3/2012 | Segawa | 600/302 |
| 8,343,038 B2* | 1/2013 | Segawa | 600/118 |
| 8,454,495 B2* | 6/2013 | Kawano et al. | 600/118 |
| 2008/0027267 A1* | 1/2008 | Segawa | 600/7 |
| 2008/0039675 A1* | 2/2008 | Segawa | 600/7 |
| 2008/0103372 A1 | 5/2008 | Segawa | |
| 2008/0257768 A1* | 10/2008 | Uchiyama | 206/350 |
| 2012/0080351 A1* | 4/2012 | Takahashi et al. | 206/528 |

FOREIGN PATENT DOCUMENTS

| | | |
|---|---|---|
| JP | 2006-187424 A | 7/2006 |
| JP | 2006-187425 A | 7/2006 |
| JP | 2006-288541 A | 10/2006 |
| JP | 2006-296492 A | 11/2006 |
| JP | 2008-289724 A | 12/2008 |
| JP | 2009-172212 A | 8/2009 |
| WO | WO 2008/053893 A1 | 5/2008 |

* cited by examiner (a)　　　　　　　　　　(b)

(a)　　　　　　　　　　　　(b)

CASING OF CAPSULE ENDOSCOPE, CAPSULE ENDOSCOPE KIT, ASSEMBLY METHOD OF CAPSULE ENDOSCOPE KIT AND ASSEMBLY DEVICE OF CAPSULE ENDOSCOPE KIT

CROSS REFERENCES TO RELATED APPLICATIONS

This application is a continuation of PCT international application Ser. No. PCT/JP2012/061906 filed on May 9, 2012, which designates the United States and which claims the benefit of priority from Japanese Patent Application No. 2011-108796 filed on May 13, 2011; the entire contents of each of which are incorporated herein by reference.

BACKGROUND OF THE INVENTION

1. Field of the Invention

The present invention relates to a casing of a capsule endoscope, a capsule endoscope kit, an assembly method of the capsule endoscope kit, and an assembly device of the capsule endoscope kit.

2. Description of the Related Art

Conventionally, in the field of endoscopes, capsule endoscopes in which an imaging function and a wireless communication function are incorporated into a capsule-shaped casing having such a size that the casing can be inserted into the digestive tract of a subject such as a patient have been developed. A capsule endoscope moves through the inside of the digestive tract according to a peristaltic motion or the like after the capsule endoscope is swallowed from the mouth of a subject. In the period in which the capsule endoscope is inserted into the digestive tract of the subject and is excreted outside the subject, the capsule endoscope sequentially acquires images (hereinafter sometimes referred to as in-vivo images) of the inside of the organs of the subject and sequentially transmits the acquired in-vivo images to a receiving device outside the subject.

The respective in-vivo images captured by the capsule endoscope are imported to an image display device via the receiving device. The image display device displays the imported in-vivo images on a display as still images or a moving image. A user such as a doctor or a nurse observes the in-vivo images of the subject displayed on the image display device and examines the inside of the organs of the subject through observation of the respective in-vivo images.

Such a capsule endoscope needs to be sterilized and maintain the sterilized state before the capsule endoscope is used for examining a subject. Therefore, conventionally, the capsule endoscope is stored in a sterilizable casing. The casing has a configuration in which an outer casing that stores an inner casing that holds the capsule endoscope is blocked by a sterilizing sheet. A hole through which an end of the capsule endoscope closer to an imaging direction is inserted along the longitudinal direction thereof is formed in the inner casing. The inner diameter of this hole is set to be slightly larger than the outer diameter of the capsule endoscope, and multiple projections are formed on the side surface of the hole. In the inner casing, the projections abut on an area of a hemispheric portion at an end portion of the capsule endoscope, which is located outside the viewing angle of an imaging optical system and located closer to a cylindrical portion, so that the capsule endoscope is fixed so as not to move in a lateral direction. Further, step portions that are provided in the inner side of the hole, have a diameter slightly smaller than the outer diameter of the capsule endoscope, and abut on an area of the hemispheric portion of the capsule endoscope over the entire circumference, located outside the optical viewing angle abuts on the capsule endoscope so that the capsule endoscope is fixed so as not to move in a longitudinal direction. In this manner, the inner casing stably holds the capsule endoscope within the hole.

In recent years, in order to image the inside of the organs of a subject with a wide viewing angle, a capsule endoscope in which a portion of the cylindrical portion as well as the hemispheric portion of the capsule-shaped casing are formed from a transparent material to increase the viewing angle of the imaging optical system has been proposed (see Japanese Patent Application Laid-open No. 2006-288541).

SUMMARY OF THE INVENTION

According to an aspect of the present invention, there is provided a casing of a capsule endoscope which includes a first casing that has a bottomed cylindrical shape and retains an imaging element therein and a transparent second casing that has a cylindrical portion and a hemispheric portion having the same outer diameter as an outer diameter of the first casing and engages with the first casing, in which at least an illumination system and a lens located on an outermost side are positioned inside the second casing, the casing including: a base portion having a planar shape; a holding portion provided at a center of the base portion so as to protrude in a direction orthogonal to a principal surface of the base portion and hold the capsule endoscope; and a plurality of abutting portions each protruding from the holding portion and abutting on at least a portion of an outer surface of the hemispheric portion of the second casing, which is located inside an optical viewing angle of the capsule endoscope and which does not contribute to generation and/or use of an image captured by the capsule endoscope to realize alignment in a longitudinal direction of the capsule endoscope.

According to an aspect of the present invention, there is provided a capsule endoscope kit including: a capsule endoscope; a casing that stores the capsule endoscope; an outer casing that holds the casing that stores the capsule endoscope therein; and a sterilizing sheet that blocks the outer casing and has sterilizing gas permeability. The capsule endoscope includes: a first casing that has a bottomed cylindrical shape and retains an imaging element therein; a second transparent casing that has a cylindrical portion and a hemispheric portion having the same outer diameter as an outer diameter of the first casing and engages with the first casing; an illumination system positioned inside the second casing; and a lens group in which at least an outermost lens is positioned inside the second casing. The casing includes: a base portion having a planar shape; a holding portion provided at a center of the base portion so as to protrude in a direction orthogonal to a principal surface of the base portion and hold the capsule endoscope; and a plurality of abutting portions each protruding from the holding portion and abutting on at least a portion of an outer surface of the hemispheric portion of the second casing, which is located inside an optical viewing angle of the capsule endoscope and which does not contribute to generation and/or use of an image captured by the capsule endoscope to realize alignment in a longitudinal direction of the capsule endoscope.

According to an aspect of the present invention, there is provided an assembly method of a capsule endoscope kit which includes a capsule endoscope that has an imaging element and a wireless communication unit and a casing that includes a base portion in which a holding portion for storing the capsule endoscope is formed and an index for alignment that is formed on a bottom surface of the holding portion or the base portion so as to align a reference position in the circumferential direction of the capsule endoscope with respect to a predetermined position in the circumferential direction of the holding portion, the assembly method including: grasping a body portion of the capsule endoscope and moving the capsule endoscope to be positioned above the holding portion so that an end in a longitudinal direction of the capsule endoscope closer to an imaging direction faces the holding portion; and aligning the reference position in the circumferential direction of the capsule endoscope with respect to the predetermined position in the circumferential direction of the holding portion by capturing an image of at least the index for alignment and inserting the capsule endoscope into the holding portion from the longitudinal direction.

According to an aspect of the present invention, there is provided an assembly device of a capsule endoscope kit for assembling the capsule endoscope kit which includes a capsule endoscope that has an imaging element and a wireless communication unit and a casing that includes a base portion in which a holding portion for storing the capsule endoscope is formed and an index for alignment that is formed on a bottom surface of the holding portion or the base portion so as to align a reference position in the circumferential direction of the capsule endoscope with respect to a predetermined position in the circumferential direction of the holding portion, the assembly device including: a grasping and moving unit for grasping a body portion of the capsule endoscope, lifting the grasped capsule endoscope about the longitudinal direction and lifting the capsule endoscope, and moving the capsule endoscope to be positioned above the holding portion so that an end in a longitudinal direction of the capsule endoscope closer to an imaging direction faces the holding portion; and a control unit for aligning the reference position in the circumferential direction of the capsule endoscope with respect to the predetermined position in the circumferential direction of the holding portion by capturing an image of at least the index for alignment and inserting the capsule endoscope into the holding portion from the longitudinal direction with respect to the grasping and moving unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
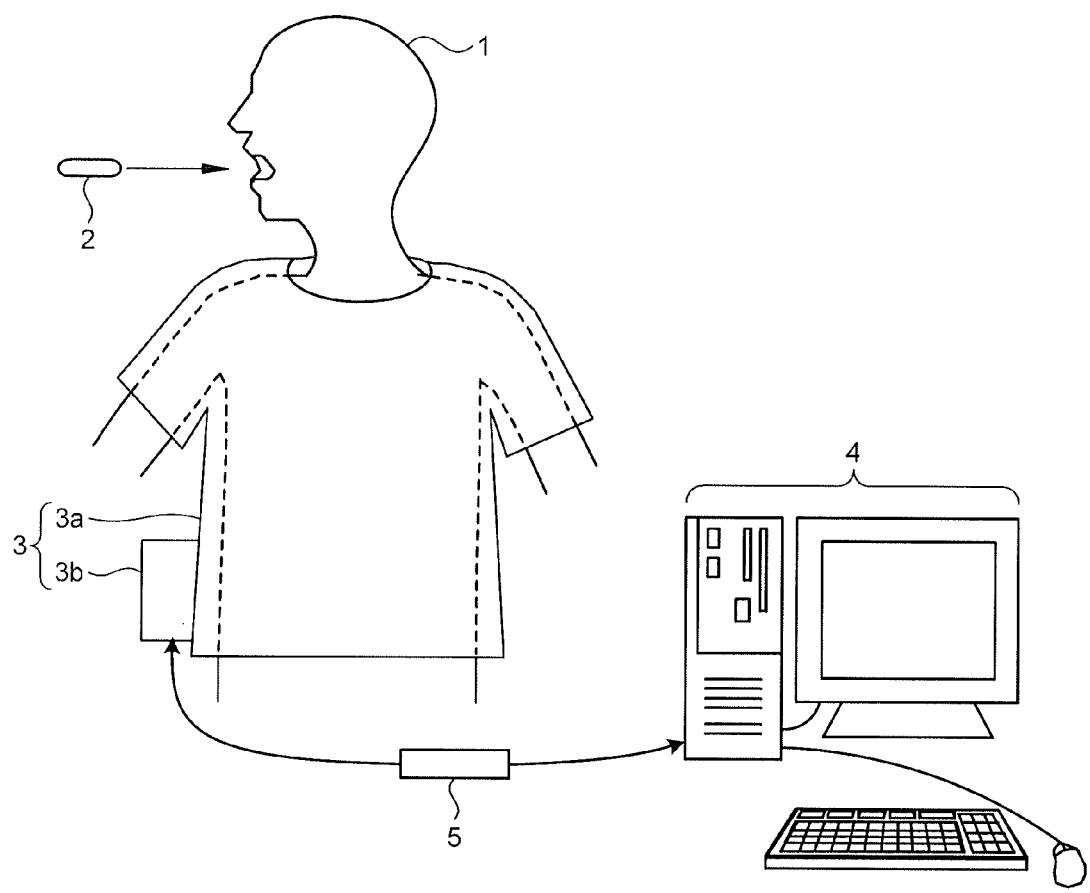
FIG. 1 is a schematic view illustrating the concept of a capsule endoscope system according to a first embodiment.

Hereinafter, a casing of a capsule endoscope, a capsule endoscope kit, an assembly method of the capsule endoscope kit, and an assembly device of the capsule endoscope, which are embodiments of the present invention, will be described with reference to the drawings. The present invention is not limited to these embodiments. In the respective drawings, the same portions are denoted by the same reference numerals. The drawings are illustrated schematically, and thus, it should be noted that the relation and ratio between the dimensions of each portion may be different from an actual case. The relation and ratio of dimensions may also be different in the respective drawings.

First, a first embodiment will be described. FIG. 1 is a schematic view illustrating the concept of a capsule endoscope system according to the first embodiment of the present invention. In FIG. 1, this capsule endoscope system includes a capsule endoscope 2, a receiving device 3, a display device 4, and a portable recording medium 5.

The capsule endoscope 2 is a swallowable capsule medical apparatus which has an imaging function and a wireless communication function and which is inserted into the body cavity of a subject 1. The receiving device 3 is an external device that is disposed outside the subject 1 and wirelessly communicates various items of information including in-vivo image information of the subject with the capsule endoscope 2. The receiving device 3 is worn on the subject 1 and includes a receiving jacket 3a that has multiple receiving antennas (not illustrated) and an external device 3b that performs signal processing or the like on the received wireless signal. The display device 4 displays an in-vivo image or the like of the subject captured by the capsule endoscope 2 based on the information received by the receiving device 3. The portable recording medium 5 performs an operation of inputting and outputting information between the receiving device 3 and the display device 4. The portable recording medium 5 has a structure such that the portable recording medium 5 can be connected to the external device 3b and the display device 4 and can output or record information when attached and connected to both. The portable recording medium 5 is inserted to the external device 3b to record information transmitted from the capsule endoscope 2 while the capsule endoscope 2 moves within the subject 1. The portable recording medium 5 is removed from the external device 3b and inserted to the display device 4 after imaging of the inside of the subject 1 by the capsule endoscope 2 ends, and the information recorded on the portable recording medium 5 is read by the display device 4.

Figure 2:
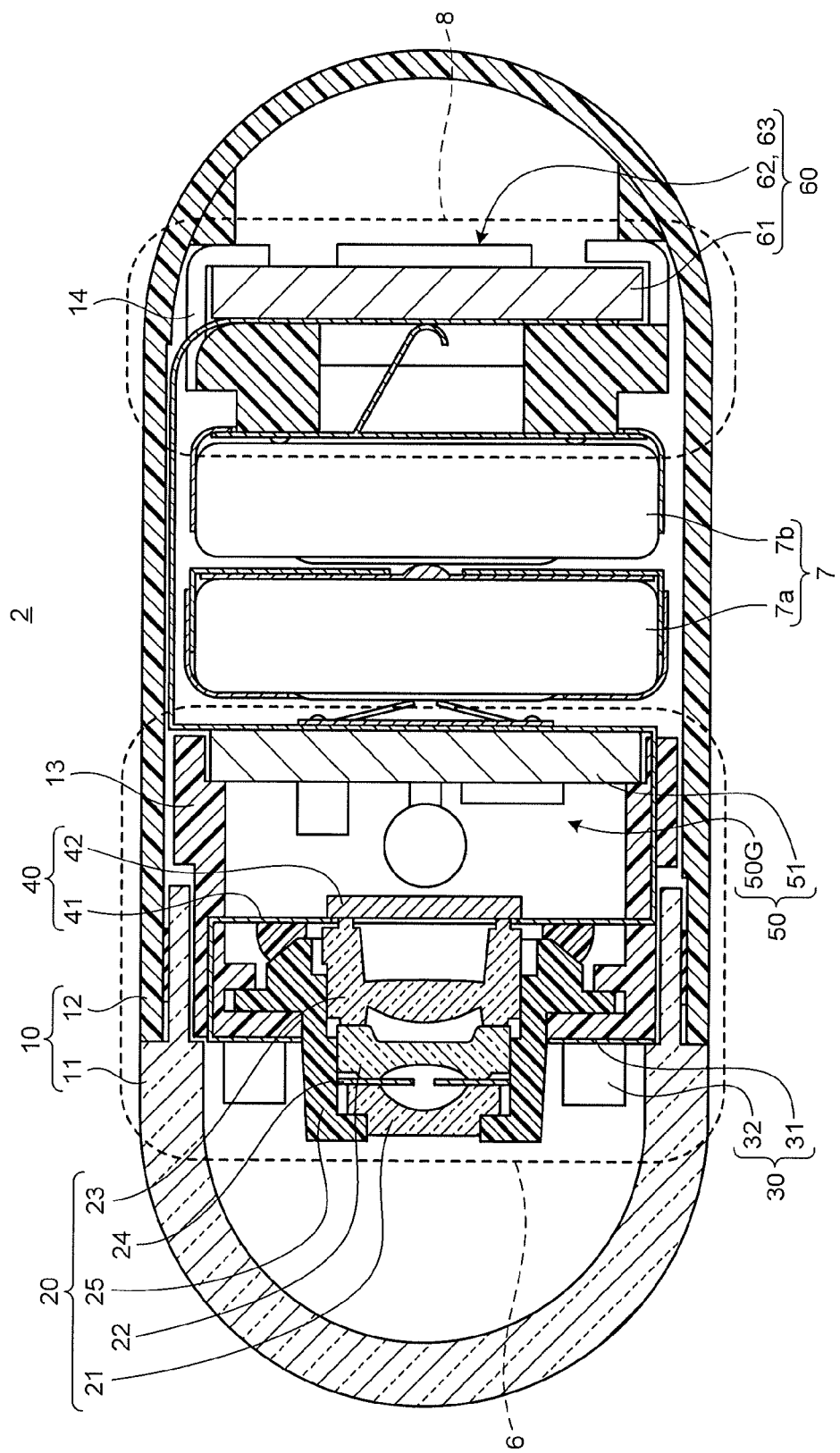
FIG. 2 is a cross-sectional view illustrating a configuration of the capsule endoscope illustrated in FIG. 1.
Figure 3:
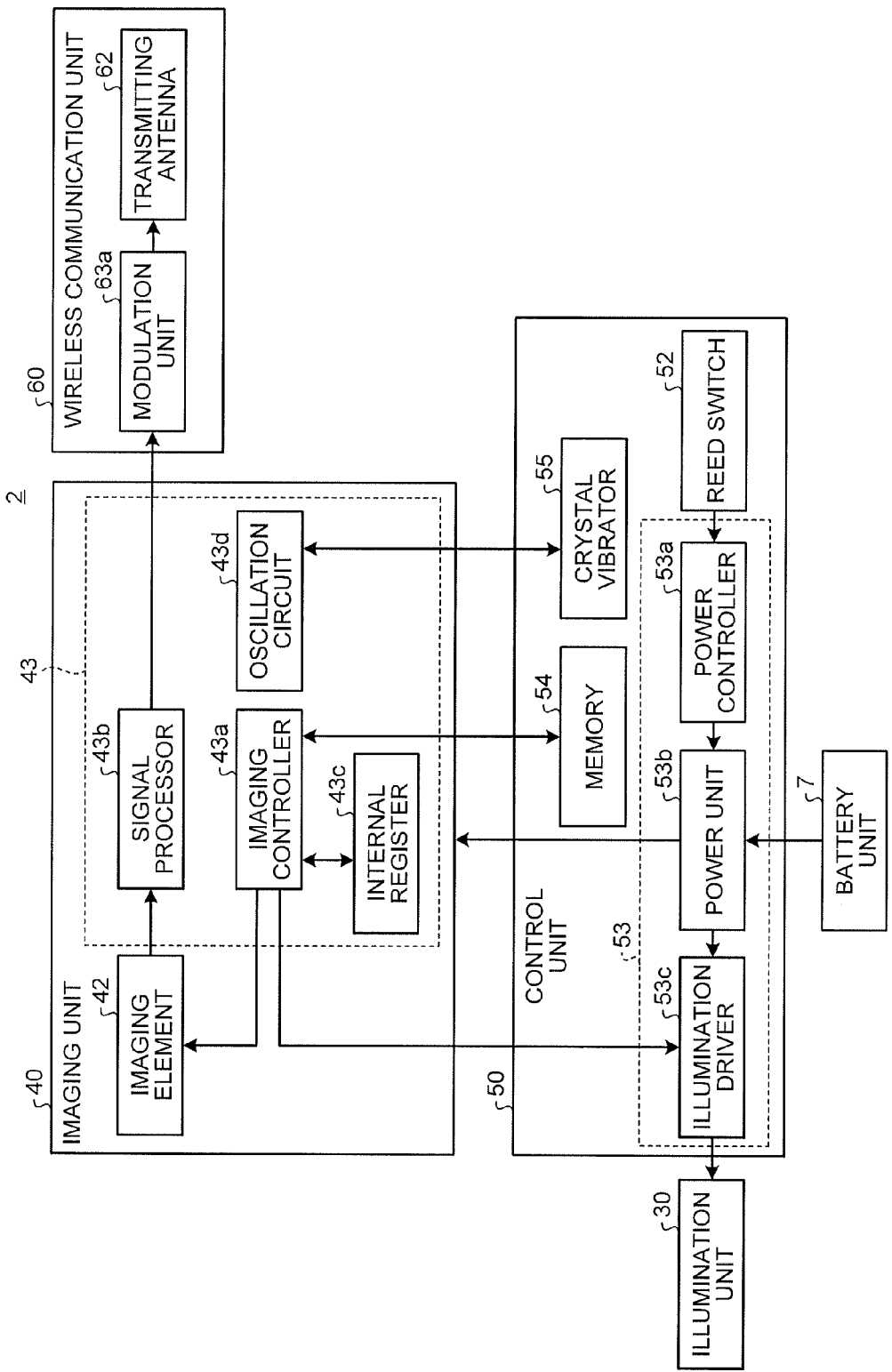
FIG. 3 is a block diagram illustrating a configuration of functional units of the capsule endoscope illustrated in FIG. 2.

FIG. 2 is a cross-sectional view illustrating a configuration of the capsule endoscope 2 illustrated in FIG. 1. FIG. 3 is a block diagram illustrating a configuration of functional units of the capsule endoscope 2 illustrated in FIG. 2.

As illustrated in FIG. 2, the capsule endoscope 2 includes a capsule-shaped casing 10 that includes a transparent dome portion 11 having a hemispheric portion and a cylindrical portion and a casing portion 12 having a bottomed cylindrical shape, a first block unit 6 in which various functional units are assembled into a spacer 13, a battery unit 7, and a second block unit 8 in which various functional units are assembled into a spacer 14. The functional units assembled into the first block unit 6 and the functional units assembled into the second block unit 8 are electrically connected. The second block unit 8, the battery unit 7, and the first block unit 6 are stored in the casing portion 12 in that order and are hermetically sealed in the casing 10 by the dome portion 11 that engages with the casing portion 12 to serve as a lid.

The first block unit 6 includes an objective lens unit 20 that collects light entering from the outside via the dome portion 11 to form an image on a light receiving portion of an imaging element 42 to be described below, an illumination unit 30 that generates illumination light for illuminating the subject 1, an imaging unit 40 that photoelectrically converts the light received via the objective lens unit 20 to generate an electrical signal that represents an image, and a control unit 50 that performs various types of control such as ON/OFF control of the power of the capsule endoscope 2. Among these units, the objective lens unit 20 is designed such that an entrance pupil position is identical to the center of the dome portion 11. The control unit 50 is electrically connected to the battery unit 7.

The battery unit 7 includes a first assembled battery 7a and a second assembled battery 7b in which batteries and contact members or the like are integrated.

The second block unit 8 includes a wireless communication unit 60 that receives the electrical signal generated by the imaging unit 40 and transmits the electrical signal to be superimposed on a wireless signal.

The objective lens unit 20 includes first to third lenses 21 to 23, a diaphragm 24, and a lens holding frame 25 that holds these optical components in alignment. The objective lens unit 20 is aligned with respect to a light receiving surface of the imaging element 42. The objective lens unit 20 and an imaging substrate 41 to be described below are fixed to each other by an adhesive. Moreover, optical components within the objective lens unit 20 are sealed by this adhesive. The objective lens unit 20 is sandwiched by the spacer 13. The first to third lenses 21 to 23 are transparent lenses which are formed by injection molding using a resin such as, for example, cycloolefin polymer (COP), polycarbonate, or acryl and are disposed so that the respective optical axes are identical to each other.

The illumination unit 30 includes a flexible illumination substrate 31 and multiple LEDs 32 which are illumination elements mounted on the illumination substrate 31. A circular opening is formed approximately at the central portion of the illumination substrate 31, and the LEDs 32 are disposed around the opening. The LEDs 32 generate white illumination light, for example. In the capsule endoscope 2, four LEDs 32 are arranged around the opening at an equal interval. These LEDs 32 are connected in series and are connected to a circuit that forms an illumination driver 53c (see FIG. 3). The position of the illumination unit 30 within the casing 10 is determined by inserting the objective lens unit 20 through the opening of the illumination substrate 31.

The imaging unit 40 includes a flexible imaging substrate 41, the imaging element 42 such as CMOS that is flip-chip mounted on the imaging substrate 41, and a circuit unit 43 (see FIG. 3) for causing the imaging element 42 to execute an imaging operation. The imaging element 42 is held inside the casing portion 12 and is arranged so that the light receiving surface faces the imaging substrate 41. The imaging element 42 receives and photoelectrically converts the light having passed through the respective lenses of the objective lens unit 20 to generate an electrical signal that represents an image. The circuit unit 43 includes an imaging controller 43a that controls the imaging operation of the imaging element 42, a signal processor 43b that performs predetermined signal processing on the electrical signal generated by the imaging element 42 to convert the electrical signal into an image signal, an internal register 43c that stores information (ID information or the like) on the capsule endoscope 2, and an oscillation circuit 43d that generates a clock signal based on vibration generated by a crystal vibrator 55 to be described below.

The control unit 50 includes a control substrate 51 formed of a rigid substrate, a reed switch 52 mounted on the control substrate 51, a power IC 53, a memory 54, and an electronic component group 50G such as a crystal vibrator 55. The reed switch 52 performs a switching operation in response to a magnetic field applied from the outside. The power IC 53 includes a power controller 53a that controls the start and stop of a power according to a switching operation of the reed switch 52, a power unit 53b that supplies power to the illumination unit 30 and the imaging unit 40 under the control of the power controller 53a, and the illumination driver 53c that drives the illumination unit 30. The memory 54 is an EEPROM, for example, and stores operation setting information or the like.

The wireless communication unit 60 includes a substrate (hereinafter referred to as a wireless substrate) 61 for wireless communication, an antenna (hereinafter referred to as a transmitting antenna) 62 for wireless signal transmission formed on the wireless substrate 61, and an electronic component 63 for wireless communication mounted on the wireless substrate 61. The electronic component 63 includes elements or the like that form a modulation unit 63a that modulates the image signal output from the imaging unit 40, for example.

Figure 4:
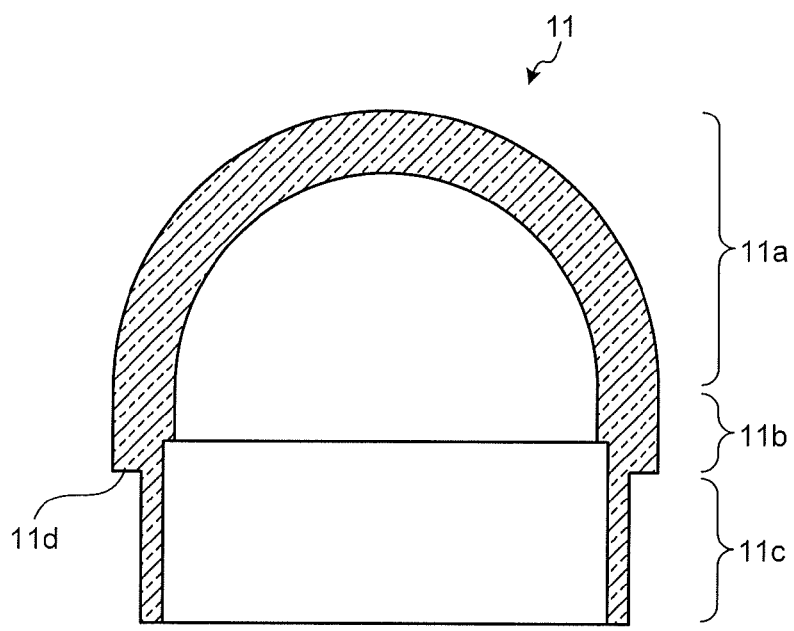
FIG. 4 is a cross-sectional view of a dome portion illustrated in FIG. 2, taken along a central axis in the longitudinal direction of a capsule endoscope.

Next, the dome portion 11 of the casing 10 will be described in detail. FIG. 4 is a cross-sectional view of the dome portion 11 taken along the central axis in the longitudinal direction of the capsule endoscope 2.

The dome portion 11 includes a hemispheric dome portion 11a having a hemispheric shape, a cylindrical dome portion 11b having a cylindrical shape having the same outer diameter as the outer diameter of the hemispheric dome portion 11a, and a dome engagement portion 11c that is notched so that the outer diameter thereof is smaller than the cylindrical dome portion 11b and that engages with the casing portion 12. A parting line that occurs during molding may be disposed at the boundary between the hemispheric dome portion 11a and the cylindrical dome portion 11b. Due to such a parting line, it is possible to visually perceive the boundary between the hemispheric dome portion 11a and the cylindrical dome portion 11b with ease.

The hemispheric dome portion 11a is a portion that becomes one end portion in the longitudinal direction of the capsule endoscope 2. A surface of an area of the hemispheric dome portion 11a belonging to the optical viewing angle range of the imaging unit 40 is mirror-polished.

The cylindrical dome portion 11b is provided so that the hemispheric dome portion 11a can be grasped without making contact with the mirror-polished portion during assembling or the like. The hemispheric dome portion 11a and the cylindrical dome portion 11b have the same outer diameter as the outer diameter of the casing portion 12.

The outer diameter of the dome engagement portion 11c is approximately the same as the inner diameter of a fitting portion of the casing portion 12. Moreover, an end surface 11d of the cylindrical dome portion 11b abuts on the end surfaces of the casing portion 12 when the dome engagement portion 11c engages with the casing portion 12. By providing such an end surface 11d, it is possible to perform accurate alignment between the dome portion 11 and the casing portion 12 in the longitudinal direction.

The dome portion 11 is formed by injection molding using a material (for example, a resin material such as polycarbonate, acryl, or cycloolefin polymer) that is transparent to the illumination light such as visible light emitted by the illumination unit 30 and has biocompatibility.

As illustrated in FIG. 2, at least the illumination unit 30, the first lens 21 located at the outermost side of the objective lens unit 20, and a portion of the lens holding frame 25 that holds the respective lenses of the objective lens unit 20 at the inside thereof are positioned inside the dome portion 11. In this manner, in the capsule endoscope 2, in order to capture a wide range of the internal areas of the organs of the subject, a portion of the cylindrical portion as well as the hemispheric portion of the capsule-shaped casing 10 are formed of a transparent material similarly to the dome portion 11 described above so that the optical viewing angle is increased.

Figure 5:
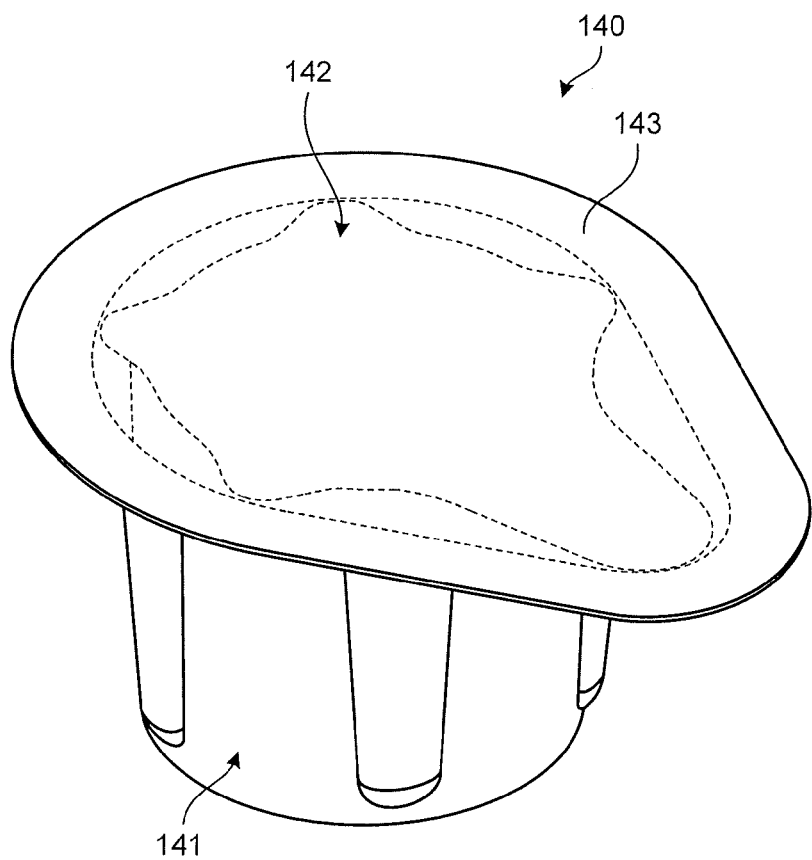
FIG. 5 is a perspective view illustrating a configuration of a package according to the first embodiment that stores the capsule endoscope illustrated in FIG. 2.
Figure 6:
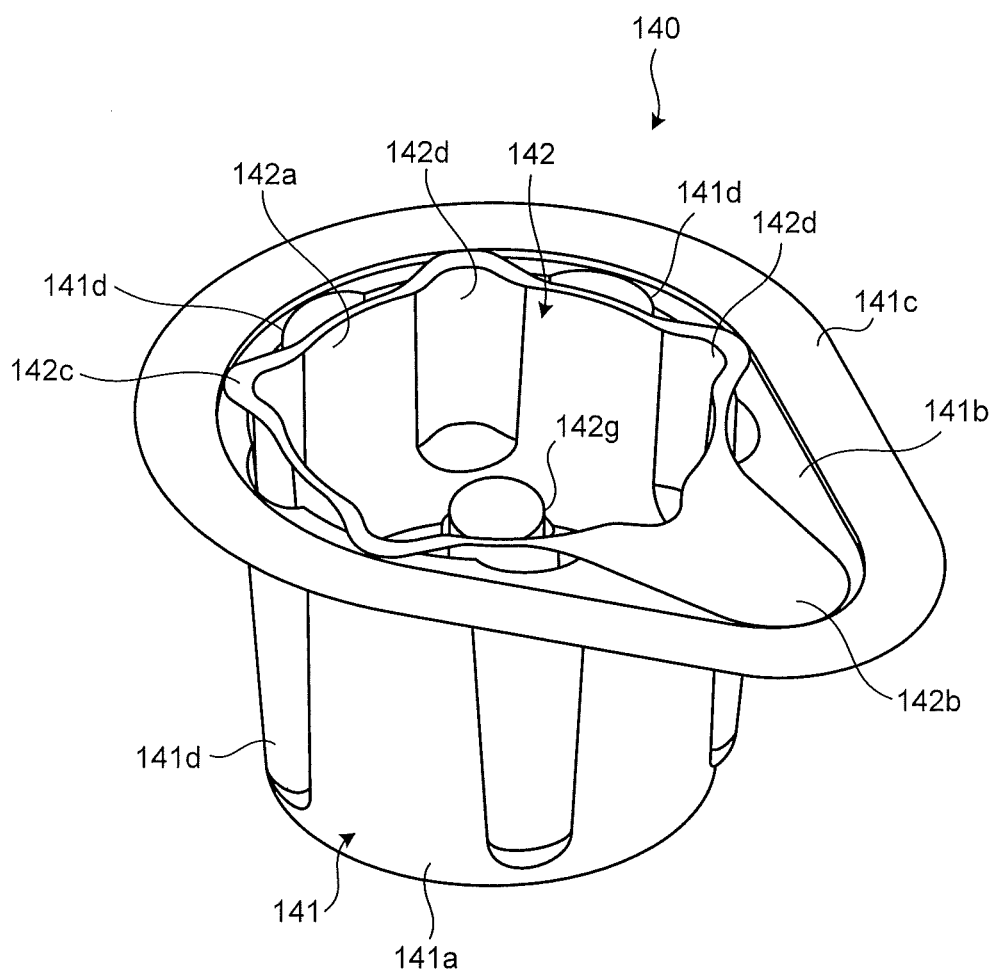
FIG. 6 is a perspective view when a sterilizing sheet is removed from the package illustrated in FIG. 5.
Figure 7:
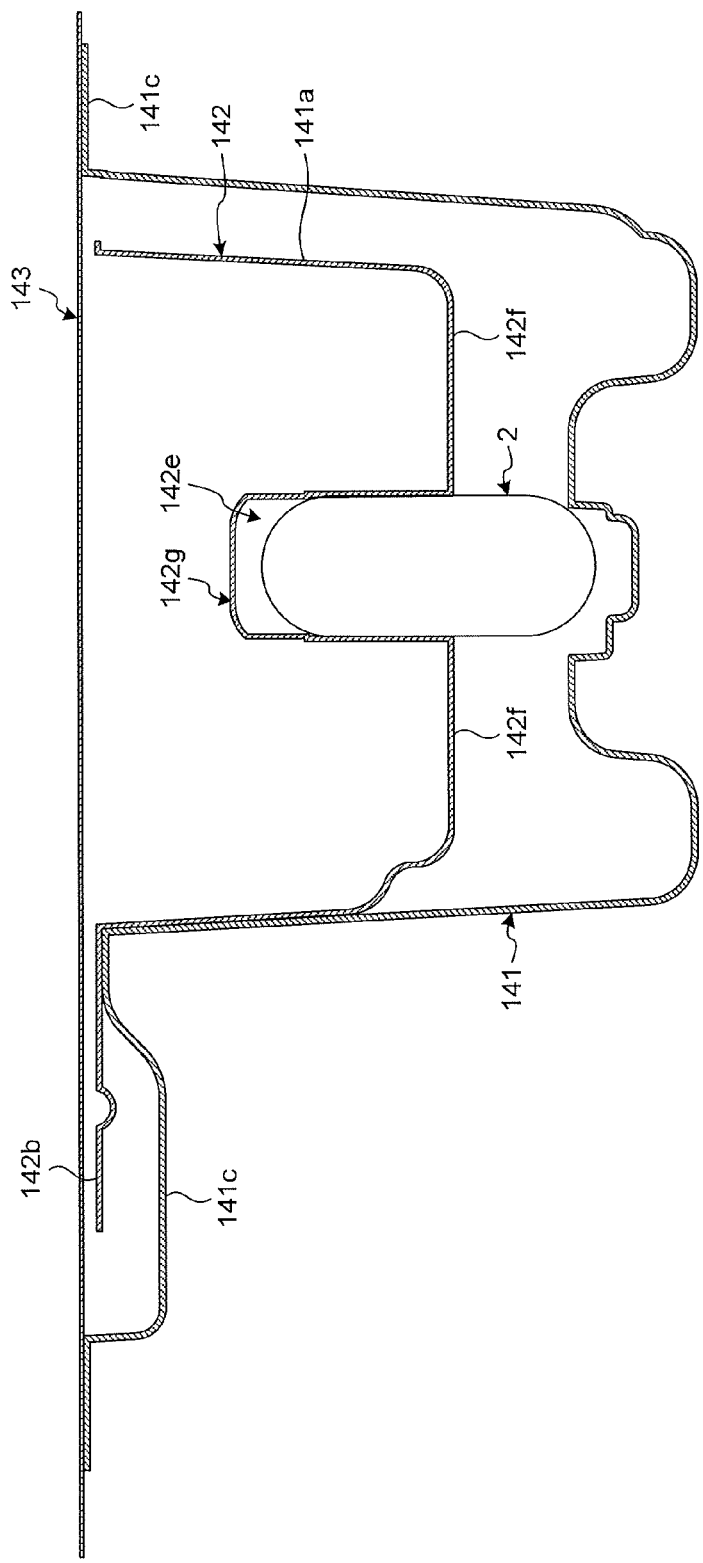
FIG. 7 is a diagram of the package illustrated in FIG. 5, taken along a plane vertical to the longitudinal direction of an outer casing.

FIG. 5 is a perspective view illustrating a configuration of a package according to the first embodiment that stores the capsule endoscope 2. FIG. 6 is a perspective view when a sterilizing sheet to be described below is removed from the package illustrated in FIG. 5. FIG. 7 is a diagram of the package illustrated in FIG. 5, taken along a plane vertical to the longitudinal direction of an outer casing to be described below.

As illustrated in FIGS. 5 to 7, a package 140 according to the first embodiment includes an outer casing 141 that is an external casing, an inner casing 142 that is fitted into the outer casing 141 and holds the capsule endoscope 2, and a sterilizing sheet 143 that is provided on an upper surface of the outer casing 141 so as to block an opening of the outer casing 141.

The outer casing 141 includes a bottomed cylindrical portion 141a, a tongue-shaped handle portion 141b provided in a portion of an upper edge of the opening of the cylindrical portion 141a, an edge portion 141c provided on the upper edge of the opening of the cylindrical portion 141a and the outer circumference of the handle portion 141b, and multiple projecting portions 141d having an approximately semi-cylindrical shape provided on a peripheral surface of the cylindrical portion 141a and formed in the longitudinal direction of the cylindrical portion 141a so as to protrude outward from the inside of the cylindrical portion 141a. The handle portion 141b is configured such that a handle portion 142b of the inner casing 142 to be described below abuts on the handle portion 141b. The edge portion 141c has a predetermined width and is provided one step above the upper edge of the opening of the cylindrical portion 141a and the outer circumference of the handle portion 141b. The sterilizing sheet 143 is attached to the upper surface of the edge portion 141c in a state where the inner casing 142 is stored in the outer casing 141.

The inner casing 142 is stored in the outer casing 141 in a state where one end in the longitudinal direction of the capsule endoscope 2 is fitted to a hole 142e with a bottom (a bottom surface 142g) formed in a base portion 142f which is a bottom portion of a cylindrical portion 142a.

Figure 8:
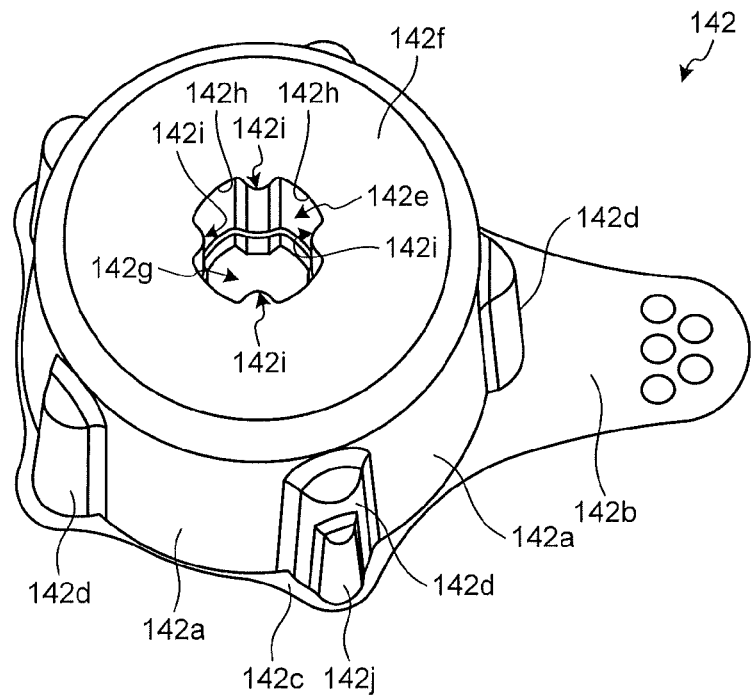
FIG. 8 is a perspective view of an inner casing illustrated in FIG. 5.
Figure 9:
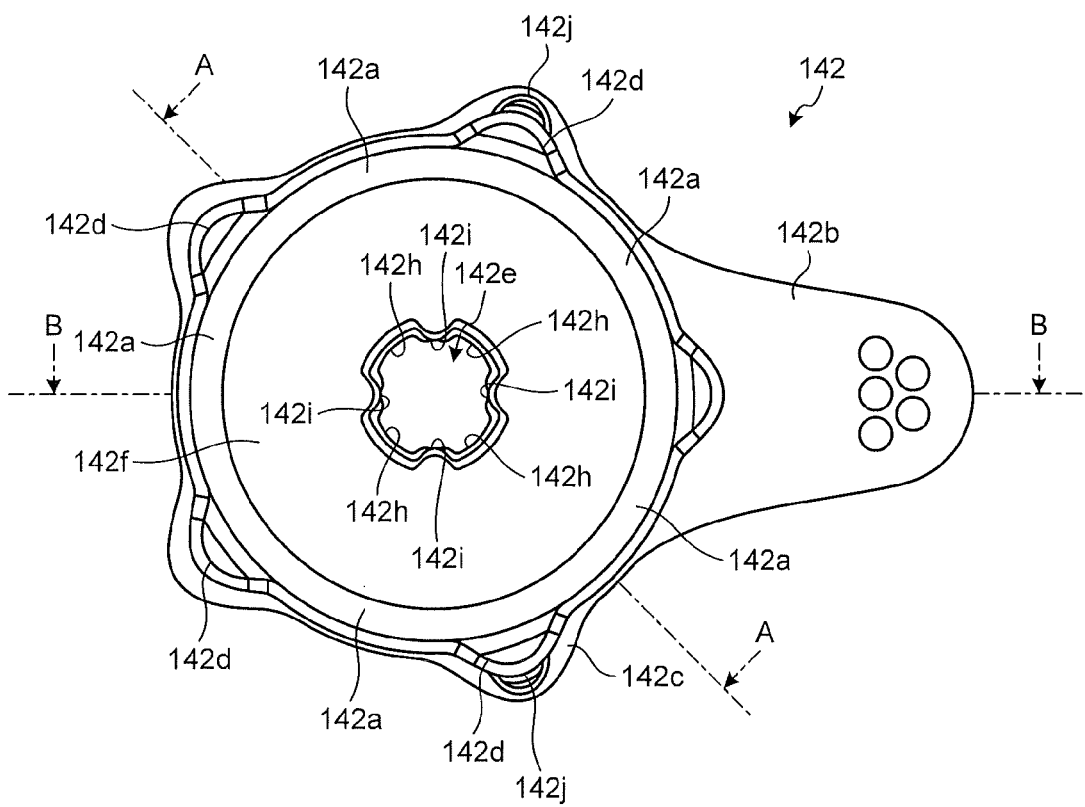
FIG. 9 is a top view illustrating an upper surface of the inner casing illustrated in FIG. 8.
Figure 10:
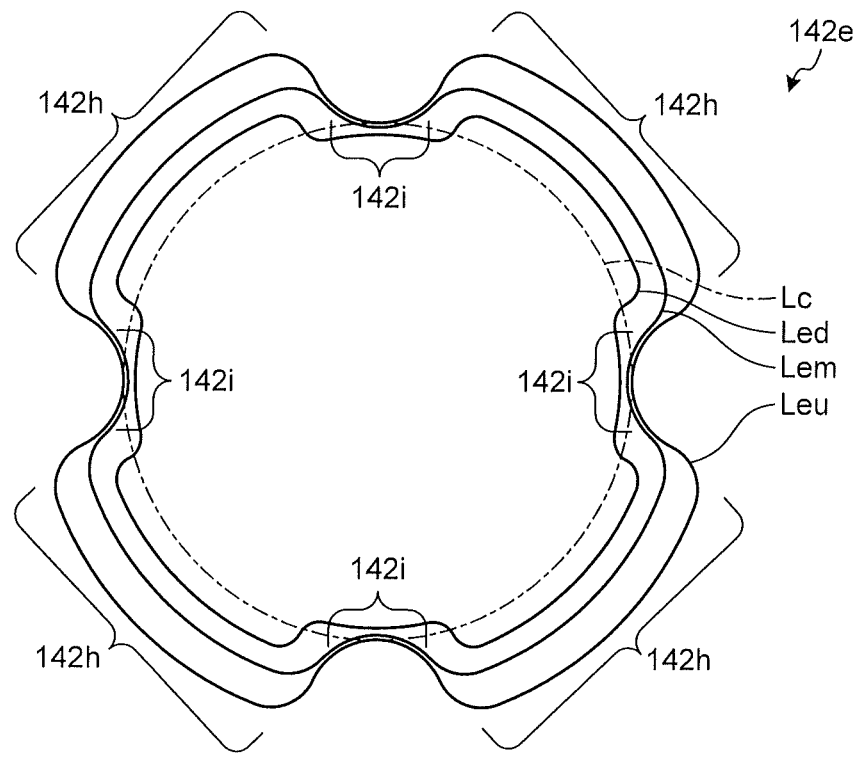
FIG. 10 is an enlarged view of a hole illustrated in FIGS. 8 and 9 when the hole is seen from above.
Figure 11:
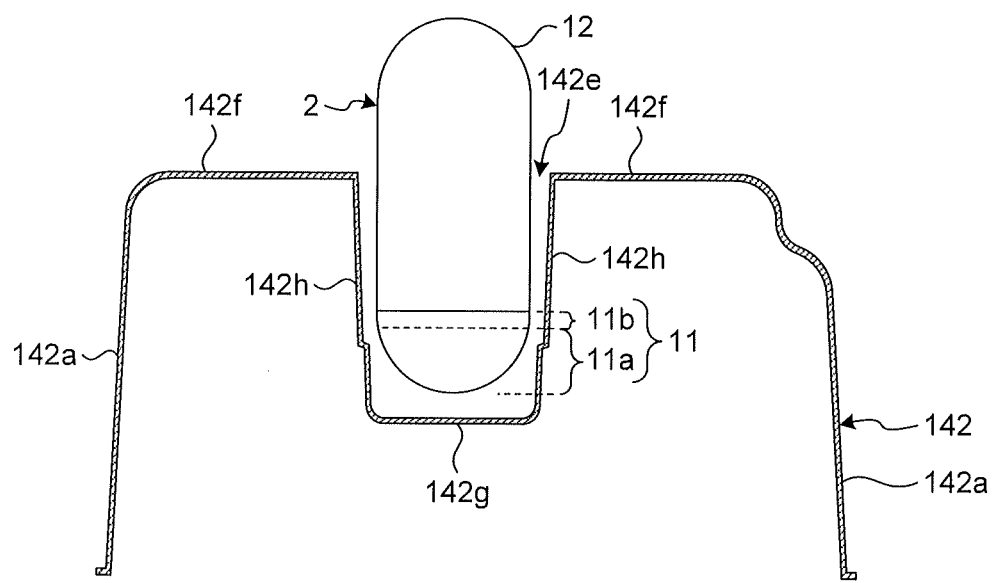
FIG. 11 is a cross-sectional view taken along line A-A illustrated in FIG. 9.
Figure 12:
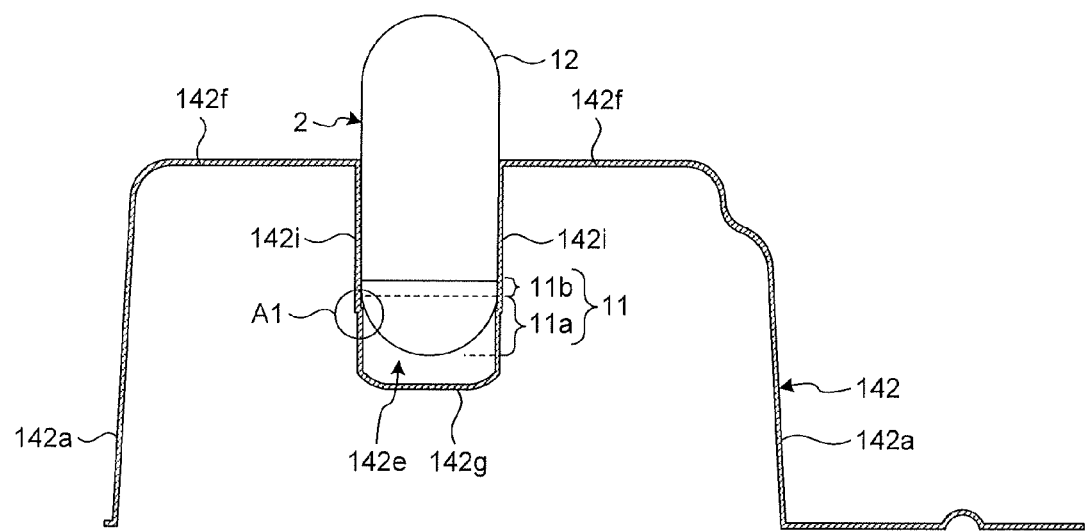
FIG. 12 is a cross-sectional view taken along line B-B illustrated in FIG. 9.
Figure 13:
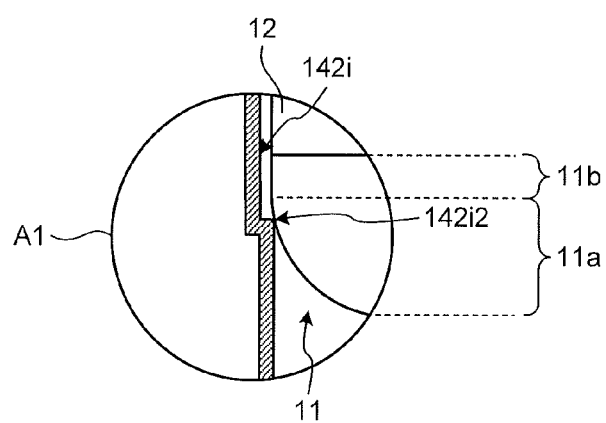
FIG. 13 is an enlarged view of an area A1 illustrated in FIG. 12.

This inner casing 142 will be described in further detail with reference to FIGS. 8 to 13. FIG. 8 is a perspective view of the inner casing illustrated in FIG. 5 and is a perspective view when the inner casing is reversed from the state illustrated in FIG. 7. FIG. 9 is a top view illustrating an upper surface of the inner casing illustrated in FIG. 8. FIG. 10 is an enlarged view of the hole 142e illustrated in FIGS. 8 and 9 when the hole is seen from above. In FIG. 10, a circle Lc indicates the outer diameter of the casing portion 12 of the capsule endoscope 2. In FIG. 10, curves Leu, Led, and Lem represent the shape of the hole 142e when seen from above, in which the curve Leu is a curve that represents the shape of an upper end portion of the hole 142e, the curve Led is a curve that represents the shape of a lower end portion of the hole 142e, and the curve Lem is a curve that represents the shape of a middle portion of the hole 142e. FIG. 11 is a cross-sectional view along line A-A illustrated in FIG. 9. FIG. 12 is a cross-sectional view along line B-B illustrated in FIG. 9. FIG. 13 is an enlarged view of an area A1 illustrated in FIG. 12.

As illustrated in FIGS. 6 and 8 to 13, the inner casing 142 includes the cylindrical portion 142a, a tongue-shaped handle portion 142b provided in a portion of an upper edge of an opening of the cylindrical portion 142a, an edge portion 142c provided on the upper edge of the opening of the cylindrical portion 142a so as to be continuous to the handle portion 142b, and multiple projecting portions 142d having an approximately semi-cylindrical shape that protrudes outward from the inside of the cylindrical portion 142a.

The base portion 142f which is a bottom surface of the cylindrical portion 142a forms a flat surface. The hole 142e that protrudes in a direction orthogonal to a principal surface of the base portion 142f and serves as a holding portion that holds the capsule endoscope 2 is formed at the center of the base portion 142f. An end portion of the capsule endoscope 2, specifically an end portion of the transparent dome portion 11, is inserted into the hole 142e.

The hole 142e is inclined inward as it advances from the upper end toward the bottom surface 142g. As indicated by the curve Lc and the curves Leu, Led, and Lem in FIG. 10, a principal side surface 142h of the hole 142e has a diameter larger than the outer diameter of the casing portion 12 of the capsule endoscope 2. The principal side surface 142h corresponds to a portion other than a protruding portion 142i and step portions 142i2 described later. Thus, the principal side surface 142h does not make contact with the side surface of the casing portion 12 as illustrated in FIG. 11 which is a cross-sectional view of the inner casing 142 taken along a cutting plane that passes through the principal side surface 142h.

The protruding portion 142i is formed in the hole 142e so as to protrude toward the central axis of the hole 142e. As indicated by the curves Lc and Leu in FIG. 10, at least the upper end of the protruding portion 142i is positioned on a circle that has a diameter slightly smaller than the outer diameter of the casing portion 12. That is, a distal end of the protruding portion 142i is positioned on a circle that has a diameter smaller than the outer diameter of the casing portion 12 of the capsule endoscope 2 so that the capsule endoscope 2 is fixed so as not to move in the lateral direction. Moreover, the protruding portion 142i makes contact with the side surface of the casing portion 12 to hold the casing portion 12 of the capsule endoscope 2 as illustrated in FIG. 12 which is a cross-sectional view of the inner casing 142 taken along a cutting plane that passes through the protruding portion 142i. The inner casing 142 is formed of a material having rigidity relatively lower than that of the casing portion 12 of the capsule endoscope 2. Thus, when the capsule endoscope 2 is stored in the inner casing 142, the distal end of the protruding portion 142i is pressed and deformed by the capsule endoscope 2. A repulsive force generated due to the deformation of the distal end of the protruding portion 142i acts on the surface of the casing portion 12 of the capsule endoscope 2, whereby movement of the capsule endoscope 2 in the lateral direction is restricted. As illustrated in FIG. 10, four protruding portions 142i are formed at an equal interval on a circumference about the hole 142e, which is located on a plane that is vertical to the central axis of the hole 142e.

Further, as illustrated in FIGS. 12 and 13, multiple step portions 142i2 each protruding further from the hole 142e are formed at positions corresponding to the formation positions of the respective protruding portions 142i. The step portions 142i2 protrude up to a circumference of a circle having approximately the same diameter as the outer diameter at a predetermined portion of the hemispheric dome portion 11a of the dome portion 11. The step portions 142i2 have a function of an abutting portion that abuts on the outer surface of the hemispheric dome portion 11a of the dome portion 11 to perform alignment in the longitudinal direction of the capsule endoscope 2. The step portions 142i2 abut on the outer surface of the hemispheric dome portion 11a with a small line width. As illustrated in FIG. 10, since the four protruding portions 142i are formed at an equal interval on a circumference about the central axis of the hole 142e, which is located on a plane that is vertical to the central axis of the hole 142e, the four step portions 142i2 are formed at an equal interval on a circumference about the central axis of the hole 142e, which is located on a plane that is vertical to the central axis of the hole 142e.

Figure 14:
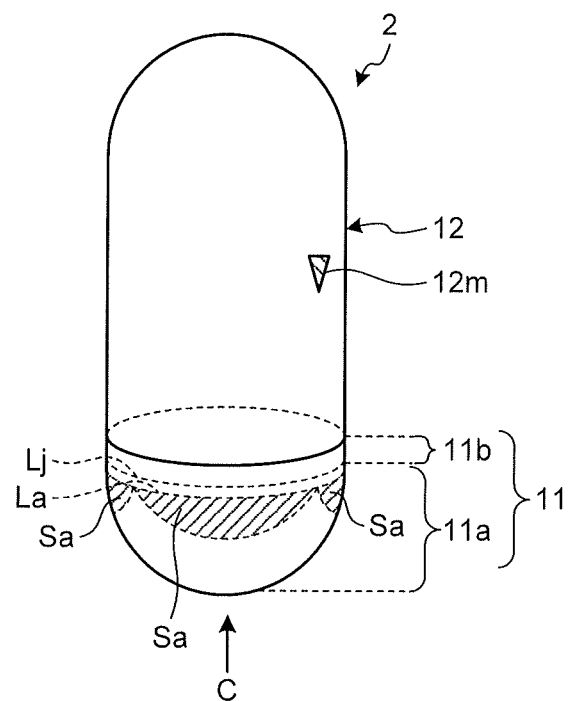
FIG. 14 is a perspective view illustrating an area of an outer surface of a hemispheric dome portion of the capsule endoscope, on which step portions of the inner casing illustrated in FIG. 9 abut.
Figure 15:
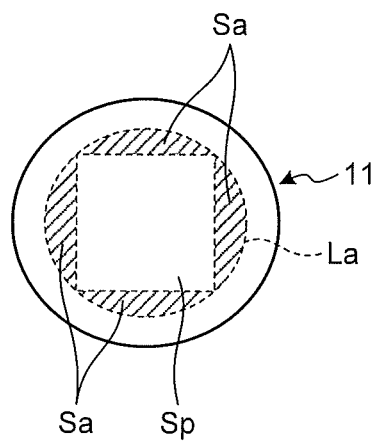
FIG. 15 is a view taken along an arrow C of FIG. 14.

In the first embodiment, the area of the outer surface of the hemispheric dome portion 11a, on which the step portions 142i2 abut, is set such that the step portions 142i2 abut on a predetermined portion of the hemispheric dome portion 11a of the dome portion 11. Therefore, an area of the hemispheric dome portion 11a, on which the step portions 142i2 abut, will be described with reference to FIGS. 14 and 15. FIG. 14 is a perspective view illustrating the area of the hemispheric dome portion 11a, on which the step portions 142i2 abut. FIG. 15 is a view taken along an arrow C of FIG. 14.

In FIGS. 14 and 15, a curve Lj is a curve that represents the boundary between the hemispheric dome portion 11a and the cylindrical dome portion 11b of the dome portion 11, and a curve La represents a curve corresponding to an optical viewing angle boundary of the capsule endoscope 2. In FIG. 15, an area Sp represents an area through which the light entering the imaging element 42 passes.

Here, in the first embodiment, the area, on which the step portions 142i2 abut, is set to the area Sa illustrated in FIGS. 14 and 15. This area Sa corresponds to an area of the outer surface of the hemispheric dome portion 11a, which is inside the curve La and is outside the area Sp. That is, the area Sa is an area of the outer surface of the hemispheric dome portion 11a, which is inside an imaging viewing angle of the imaging optical system of the capsule endoscope 2 and is outside an area through which the light entering the imaging element 42 passes.

Since this area Sa is outside the area through which the light entering the imaging element 42 passes although it is inside the viewing angle of the capsule endoscope 2, this area Sa corresponds to an area that does not contribute to generation of an image captured by the capsule endoscope 2.

Thus, even when the step portions 142i2 abut on this area Sa so that a scratch is formed in a portion of the outer surface of the hemispheric dome portion 11a located inside the viewing angle, since the area Sa is not an area through which the light entering the imaging element 42 of the capsule endoscope 2 passes, the scratch may not be included in the image captured by the capsule endoscope 2. Moreover, in the first embodiment, since the step portions 142*i*2 abut on the predetermined area Sa of the outer surface of the hemispheric dome portion 11*a*, it is possible to appropriately perform alignment in the longitudinal direction of the capsule endoscope 2. Thus, the capsule endoscope 2 may not move in the longitudinal direction, and the capsule endoscope 2 can be stably held within the inner casing 142.

Moreover, in the first embodiment, since the area, on which the step portions 142*i*2 abut, is set to the area Sa illustrated in FIGS. 14 and 15, the step portions 142*i*2 are formed at an equal angular interval on a circumference of a circle that has approximately the same diameter as the outer diameter at a predetermined portion of the hemispheric dome portion 11*a* included in the area Sa. Thus, even if a shift corresponding to the equal angular interval occurs when the capsule endoscope 2 is inserted into the hole 142*e* of the inner casing 142, since the step portions 142*i*2 do not make contact with the area of the hemispheric dome portion 11*a*, through which the light entering the imaging element 42 passes, it is possible to reliably perform alignment in the longitudinal direction. Thus, the workability of an operation of inserting the inner casing 142 of the capsule endoscope 2 into the hole 142*e* is improved.

As described above, in the first embodiment, since the area, on which the step portions 142*i*2 abut, is set to the area Sa, the capsule endoscope 2 in which a portion of the cylindrical dome portion 11*b* as well as the hemispheric dome portion 11*a* are formed of a transparent material to increase the viewing angle can be stably held within the inner casing 142 in a state where the function of imaging the subject 1 is appropriately maintained.

In the inner casing according to the first embodiment, as illustrated in FIGS. 8 and 9, a small projecting portion 142*j* having an approximately cylindrical shape that protrudes further outward from the projecting portion 142*d* is provided in any one of the multiple projecting portions 142*d*. In the inner casing 142, the small projecting portion 142*j* serves as a stopper in such a manner that when multiple inner casings 142 are stacked when the manufactured inner casings 142 are conveyed, for example, the front surface of one small projecting portions 142*j* abuts on the rear surface of another small projecting portion 142*j* before the bottom surfaces 142*g* of the holes 142*e*, the principal side surfaces 142*h*, the protruding portions 142*i*, and the step portions 142*i*2 of the stacked adjacent inner casings 142 make contact with each other. Thus, the adjacent inner casings 142 do not come further closer to each other. As a result, the inner casings 142 can be stacked in a state where a predetermined gap is maintained between the bottom surfaces 142*g*, the principal side surfaces 142*h*, the protruding portions 142*i*, and the step portions 142*i*2 of the adjacent inner casings 142. Thus, the shapes of the portions that hold the capsule endoscope 2, such as the bottom surface 142*g*, the principal side surface 142*h*, the protruding portion 142*i*, and the step portion 142*i*2 may not change. A protruding portion that serves as a stopper may be formed in the base portion 142*f* instead of the small projecting portion 142*j*. This protruding portion may protrude upward or downward in the vertical direction as long as the protruding portion protrudes in the vertical direction of the base portion 142*f*.

Moreover, as illustrated in FIG. 14, a marker 12*m* that indicates a reference position of the casing portion 12 of the capsule endoscope 2 in the circumferential direction of the capsule endoscope 2 may be formed in order to align the reference position in the circumferential direction of the capsule endoscope 2 to a predetermined position in the circumferential direction of the hole 142*e* of the inner casing 142. The capsule endoscope 2 may be inserted into the hole 142*e* while aligning the marker 12*m* to the predetermined position in the circumferential direction of the hole 142*e* of the inner casing 142 so that the step portions 142*i*2 appropriately abut on the area Sa. The numbers of markers 12*m* and predetermined positions in the circumferential direction of the hole 142*e* are not limited to one, but multiple markers 12*m* and multiple predetermined positions may be provided according to the position and the number of step portions 142*i*2.

Further, the capsule endoscope 2 includes the reed switch 52 that is turned on according to a magnetic force, and the power is turned on when a starter that generates a magnetic field approaches in the axial direction of the reed of the reed switch 52 from a predetermined direction. Thus, it is not possible to turn on the power of the capsule endoscope 2 unless the starter of the capsule endoscope 2 approaches in the axial direction of the reed of the reed switch 52 inside the capsule endoscope 2 from a predetermined direction. Thus, one marker 12*m* is assigned to a position corresponding to the axial direction of the reed of the reed switch 52 inside the capsule endoscope 2 as the reference position in the circumferential direction of the capsule endoscope 2, and a position corresponding to the approaching position of the starter is set as the predetermined position in the circumferential direction of the hole 142*e* of the inner casing 142. Subsequently, the capsule endoscope 2 may be inserted into the hole 142*e* while aligning the marker 12*m* to the predetermined position in the circumferential direction of the hole 142*e* so that the step portions 142*i*2 appropriately abut on the area Sa of the hemispheric dome portion 11*a* of the capsule endoscope 2, and the starter can approach accurately in the axial direction of the reed of the reed switch 52 of the capsule endoscope 2.

Moreover, in the first embodiment, an example in which the four protruding portions 142*i* and the four step portions 142*i*2 are formed on the circumference about the center of the hole 142*e*, which is located on a plane that is vertical to the central axis of the hole 142*e* has been described. However, it is sufficient to form at least two protruding portions and at least two step portions as long as the capsule endoscope 2 can be held.

Figure 16:
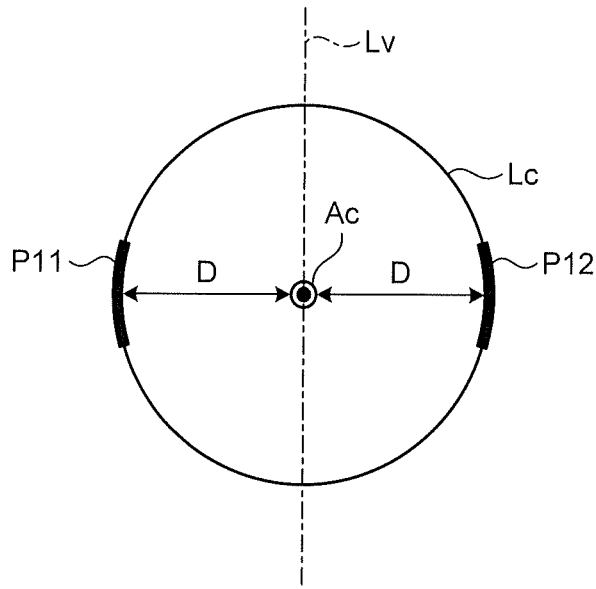
FIG. 16 is a diagram illustrating another example of the step portions of the inner casing illustrated in FIG. 9.
Figure 17:
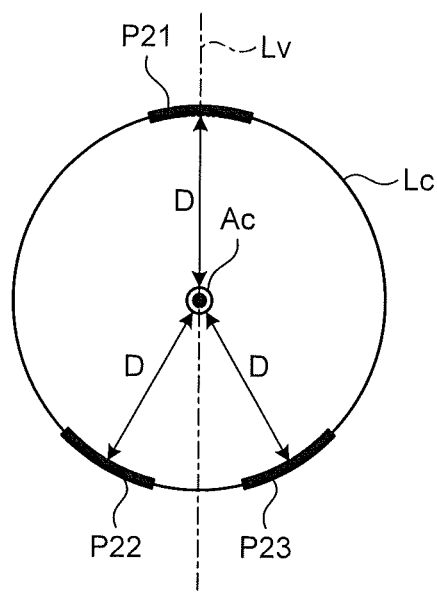
FIG. 17 is a diagram illustrating another example of the step portions of the inner casing illustrated in FIG. 9.
Figure 18:
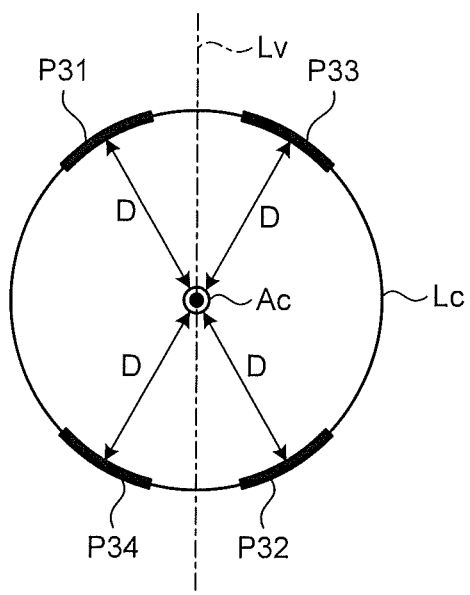
FIG. 18 is a diagram illustrating another example of the step portions of the inner casing illustrated in FIG. 9.

Moreover, in the first embodiment, although a case where the multiple protruding portions 142*i* and multiple step portions 142*i*2 are formed at an equal interval, that is, at an rotation angle other than 360°, on the circumference about the central axis of the hole 142*e*, located on a plane that is vertical to the central axis of the hole 142*e* has been described as an example, the present invention is naturally not limited to this. It is sufficient that multiple step portions 142*i*2 are formed at positions which are located at an equal distance from the central axis of the hole 142*e* and are line symmetrical to a predetermined straight line on a plane that is vertical to the central axis of the hole 142*e*. A specific example will be described with reference to FIGS. 16 to 18. FIGS. 16 to 18 are diagrams illustrating another example of the step portion of the inner casing illustrated in FIG. 9, and are schematic views of a middle portion of the hole 142*e*, taken along a plane orthogonal to the insertion direction of the capsule endoscope 2. In FIGS. 16 and 17, for the sake of reference, a circle Lc that represents the outer diameter of the casing portion 12 of the capsule endoscope 2 of the capsule endoscope 2 is illustrated.

For example, as illustrated in FIG. 16, the step portions 142*i*2 may be formed at two positions P11 and P12 which are at an equal distance D from the central axis Ac of the hole 142e and are line symmetrical to a predetermined straight line Lv on a plane that is vertical to the central axis Ac of the hole 142e. Moreover, as illustrated in FIG. 17, the step portions 142i2 may be formed at three positions, that is, one position P21 on the straight line Lv and two positions P22 and P23 which are at an equal distance D from the central axis Ac of the hole 142e and are line symmetrical to the straight line Lv. Further, as illustrated in FIG. 18, the step portions 142i2 may be formed at four positions, that is, positions P31 and P32 and positions P33 and P34 which are respectively at an equal distance D from the central axis Ac of the hole 142e and are line symmetrical to the straight line Lv, respectively.

In this manner, when multiple step portions 142i2 are formed at positions which are at an equal distance from the central axis of the hole 142e and are line symmetrical to a predetermined straight line on a plane that is vertical to the central axis of the hole 142e, the force applied from the step portions 142i2 to the capsule endoscope 2 is cancelled on the plane that is vertical to the central axis Ac. Thus, in this case, since the force applied from the step portions 142i2 to the capsule endoscope 2 is appropriately distributed, when the alignment in the longitudinal direction of the capsule endoscope 2 is performed, the capsule endoscope 2 may not be tilted so that the step portion 142i2 does not abut on an area other than the area Sa of the hemispheric dome portion 11a and a scratch is not formed.

Figure 19:
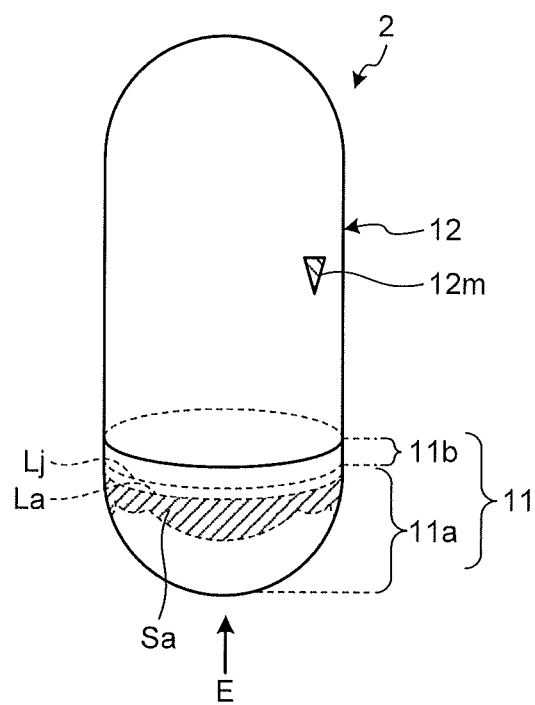
FIG. 19 is a perspective view illustrating another example of an area of an outer surface of a hemispheric dome portion of the capsule endoscope, on which step portions of the inner casing illustrated in FIG. 9 abut.
Figure 20:
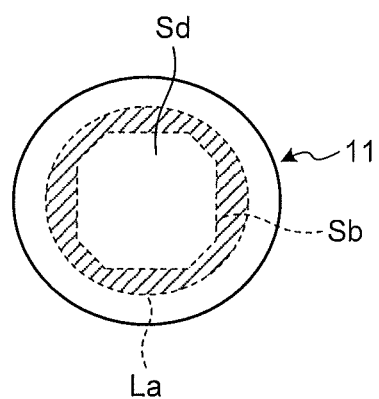
FIG. 20 is a view taken along an arrow E of FIG. 19.

Moreover, in the first embodiment, although a case where an area that does not contribute to generation of an image captured by the capsule endoscope 2 is used as the area of the hemispheric dome portion 11a, on which the step portions 142i2 abut has been described, the present invention is not limited to this. For example, when the image of the capsule endoscope 2 displayed on the display device 4 is a partial area that includes a central portion of the entire image, the area of the hemispheric dome portion 11a, on which the step portions 142i2 abut may be set such that the step portions 142i2 abut on an area of the outer surface of the hemispheric dome portion 11a corresponding to a portion which is not displayed on the display device 4. A specific example will be described with reference to FIGS. 19 and 20. FIG. 19 is a perspective view illustrating another example of the area of the hemispheric dome portion 11a, on which the step portions 142i2 abut. FIG. 20 is a view taken along an arrow E of FIG. 19.

For example, when the display device 4 displays an image in such an octagonal shape that the four corners of a rectangular image captured by the capsule endoscope 2 are notched by a predetermined amount, an area of the outer surface of the hemispheric dome portion 11a corresponding to the octagon which is a display shape of the image becomes an area Sd. In this case, the area, on which the step portions 142i2 abut, is set to an area Sb illustrated in FIGS. 18 and 19. This area Sb corresponds to an area of the outer surface of the hemispheric dome portion 11a, which is located inside the curve La and is outside the area Sd. That is, the area Sb corresponds to an area of the outer surface of the hemispheric dome portion 11a, which is located inside the optical viewing angle of the capsule endoscope 2 and which corresponds to a portion which is not displayed on the display device 4 when the image captured by the capsule endoscope 2 is displayed on the display device 4.

Since this area Sb is an area that corresponds to a portion other than the portion of the image displayed on the display device 4 even if the area Sb is located inside the optical viewing angle of the capsule endoscope 2, this area Sb corresponds to an area that does not contribute to the use of the image captured by the capsule endoscope 2.

Thus, even when the step portions 142i2 abut on this area Sb so that a scratch is formed in a portion of the outer surface of the hemispheric dome portion 11a corresponding to the inside of the viewing angle, since this area Sb is not an area which is actually displayed as an image on the display device 4, the scratch may not be included in the image captured by the capsule endoscope 2. Moreover, in this case, since the step portions 142i2 abut on the predetermined area Sb of the outer surface of the hemispheric dome portion 11a, it is possible to stably hold the capsule endoscope 2 within the inner casing 142 while appropriately performing alignment in the longitudinal direction of the capsule endoscope 2.

In this manner, even when the area, on which the step portions 142i2 abut, is set to the area Sb, it is possible to stably hold the capsule endoscope 2, of which the viewing angle is increased, within the inner casing 142 in a state where the function of imaging the subject is appropriately maintained.

Next, a second embodiment will be described. In the second embodiment, an index for alignment between a step portion and an area of an outer surface of a hemispheric dome portion, on which the step portions abut, is provided on an inner casing so that the step portions appropriately abut on a predetermined area.

Figure 21:
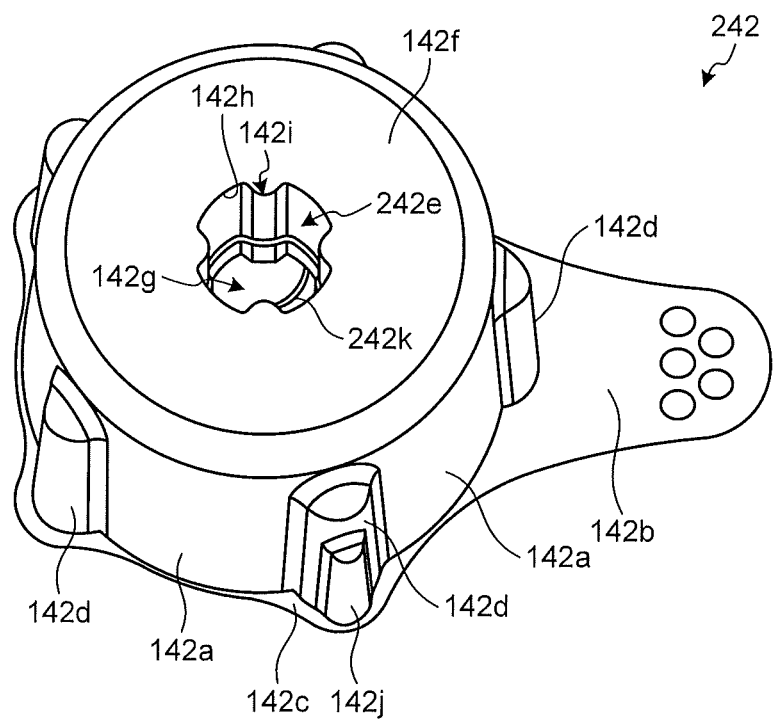
FIG. 21 is a perspective view of an inner casing according to a second embodiment.
Figure 22:
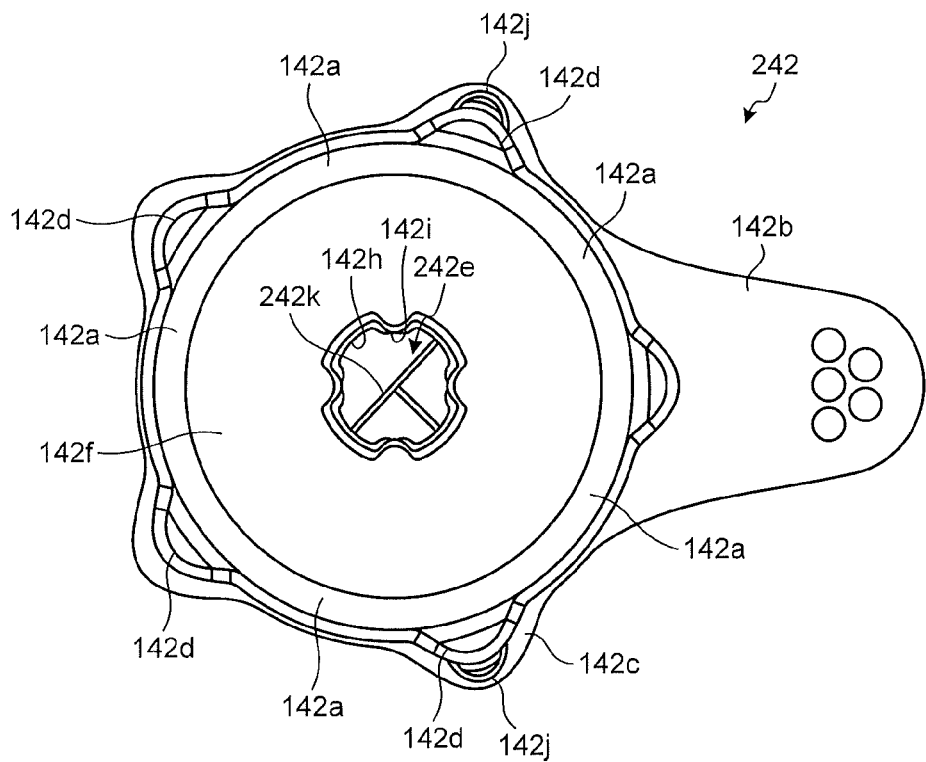
FIG. 22 is a top view illustrating an upper surface of the inner casing illustrated in FIG. 21.
Figure 23:
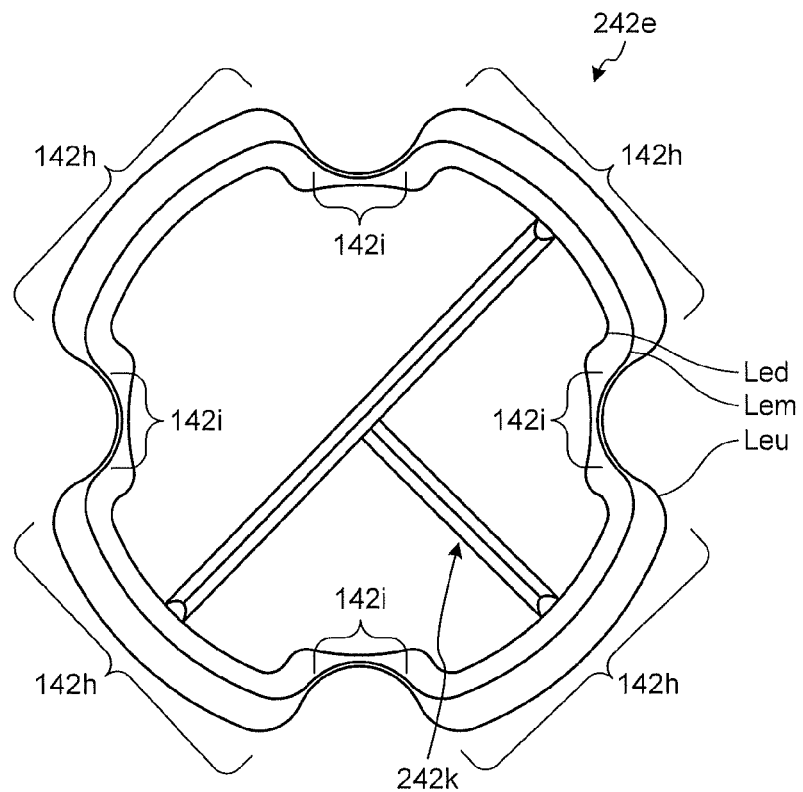
FIG. 23 is an enlarged view of a hole illustrated in FIGS. 21 and 22 when the hole is seen from above.

FIG. 21 is a perspective view of an inner casing according to the second embodiment. FIG. 22 is a top view illustrating an upper surface of the inner casing illustrated in FIG. 21. FIG. 23 is an enlarged view of a hole illustrated in FIGS. 21 and 22 when the hole is seen from above.

As illustrated in FIGS. 21 to 23, a hole 242e of an inner casing 242 according to the second embodiment has the same configuration as the hole 142e of the inner casing 142 according to the first embodiment, except that a T-shaped mark 242k which is a T-shaped index is further formed on a bottom surface.

The T-shaped mark 242k functions as an index for alignment between step portions 142i2 of the hole 242e and the area Sa or Sb of the outer surface of the hemispheric dome portion 11a of the capsule endoscope 2, on which the step portions 142i2 abut. Moreover, the T-shaped mark 242k also functions as an index for alignment between the reference position in the circumferential direction of the capsule endoscope 2 and the predetermined position in the circumferential direction of the hole 242e of the inner casing 242. Moreover, as described above, when the position corresponding to the axial direction of the reed of the reed switch 52 inside the capsule endoscope 2 is set as the reference position in the circumferential direction of the capsule endoscope 2, and a short-axis end of the T-shaped mark 242k is set so as to correspond to the approaching position of the starter as the predetermined position in the circumferential direction of the hole 242e of the inner casing 242, the T-shaped mark 242k may also function as an index for allowing the starter to accurately approach in the axial direction of the reed of the reed switch 52 of the capsule endoscope 2.

For example, as illustrated in FIG. 14, when the marker 12m that indicates the reference position in the circumferential direction of the capsule endoscope 2 is formed on the outer surface of the casing portion 12 of the capsule endoscope 2, if the capsule endoscope 2 is inserted into the hole 242e so that the marker 12m faces the short-axis end of the T-shaped mark 242k, the directions of the long and short axes of the T-shaped mark 242k are set so that the step portions 142i2 properly abut on the above-described area Sa or Sb of the hemispheric dome portion 11a of the capsule endoscope 2. Further, when the capsule endoscope 2 is inserted into the hole 242 so that the marker 12m faces the short-axis end of the T-shaped mark 242k, the directions of the long and short axes of the T-shaped mark 242k are set so that the axial direction of the reed of the reed switch 52 of the capsule endoscope 2 accurately faces a direction corresponding to the approaching position of the starter.

Moreover, even when a marker for alignment with the T-shaped mark 242k is not formed on the outer surface of the capsule endoscope 2, it is possible to appropriately perform alignment between the step portions 142i2 and the above-described area Sa or Sb of the hemispheric dome portion 11a of the capsule endoscope 2 by using the T-shaped mark 242k.

Figure 24:
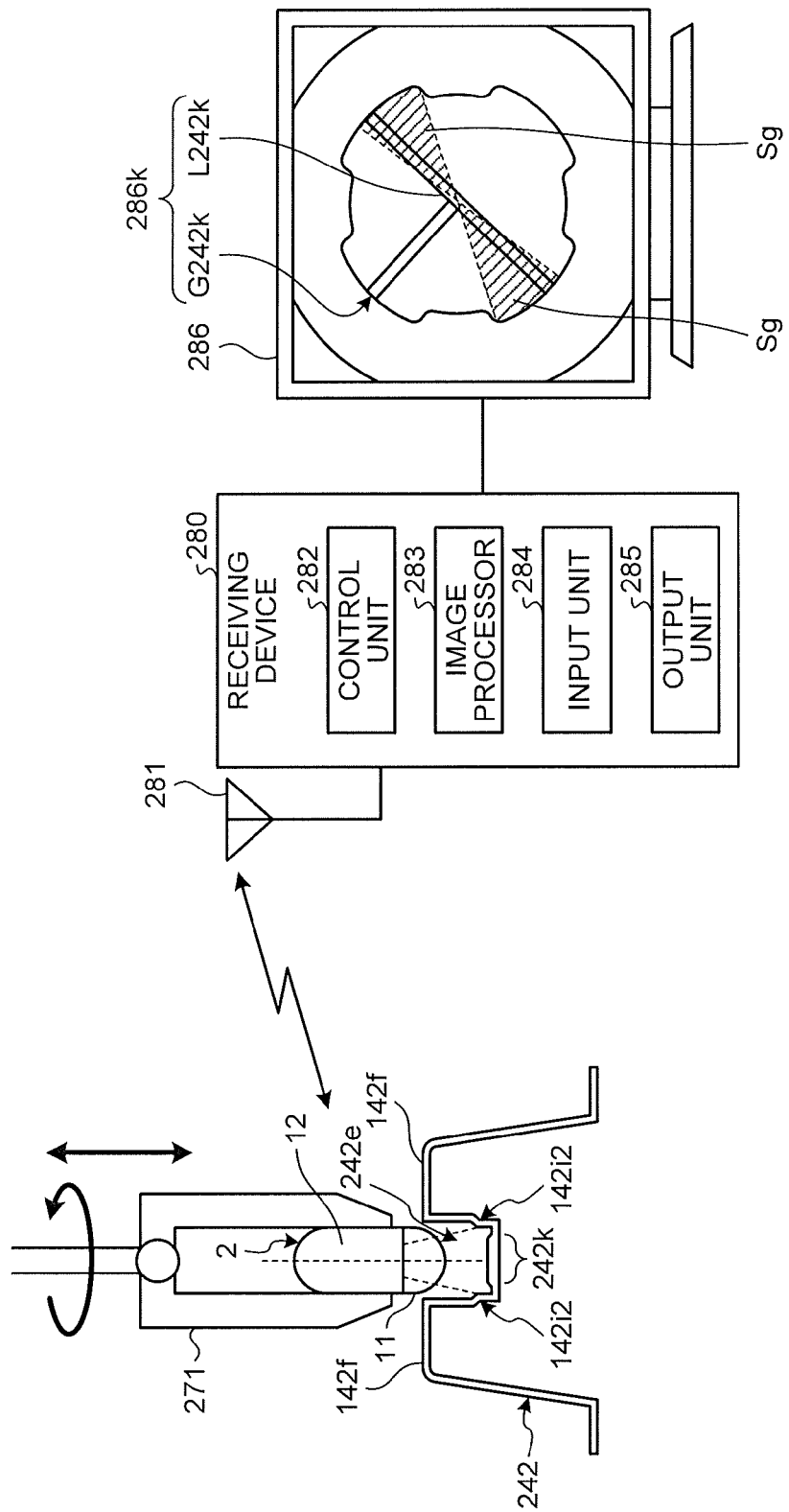
FIG. 24 is a schematic view illustrating alignment between the capsule endoscope illustrated in FIG. 2 and the inner casing illustrated in FIG. 21.

A specific example will be described with reference to FIG. 24. FIG. 24 is a schematic view illustrating alignment between the capsule endoscope 2 and the inner casing 242. As illustrated in FIG. 24, in this case, a jig 271 which is a grasping and moving portion that grasps a body portion of the capsule endoscope 2, rotates the capsule endoscope 2 about the longitudinal direction, and is capable of lifting and lowering the capsule endoscope 2 and a receiving device 280 that can receive wireless information transmitted from the capsule endoscope 2 are used.

The receiving device 280 includes an antenna 281 that receives information including the image information wirelessly transmitted from the capsule endoscope 2 to acquire images captured by the capsule endoscope 2, a control unit 282 that controls each unit of the receiving device 280, an image processor 283 that processes the image information within the received information by the antenna 281, an input unit 284 that receives instruction information regarding a processing operation of the receiving device 280 and input the instruction information to the control unit 282, an output unit 285 that outputs information on alignment in a form of sound or light under the control of the control unit 282, and a display 286 that displays images captured by the capsule endoscope 2 under the control of the control unit 282.

First, an operator moves the starter closer to the capsule endoscope 2 to turn on the power of the capsule endoscope 2, grasps the casing portion 12 which is a body portion of the capsule endoscope 2 using the jig 271, and moves the capsule endoscope 2 to be located above the hole 242e so that an end in the longitudinal direction of the capsule endoscope 2 closer to the imaging direction, that is, an end portion of the dome portion 11 faces the hole 242e of the inner casing 242. The capsule endoscope 2 captures the image of the T-shaped mark 242k formed on the bottom surface of the hole 242e and wirelessly transmits information including the captured image information. In the receiving device 280, after the image information within the information transmitted from the capsule endoscope 2, received by the antenna 281 is processed by the image processor 283, a mark image 286k of the T-shaped mark 242k captured by the capsule endoscope 2 is displayed on the display 286.

Here, a reference area Sg is displayed on the display 286 so that the reference position in the circumferential direction of the capsule endoscope 2 and the predetermined position in the circumferential direction of the hole 242e can maintain a predetermined positional relation. The reference area Sg displayed on the display is set according to an installed state of the inner casing 242 so that the step portions 142i2 of the inner casing 242 can appropriately abut on the area Sa or Sb of the capsule endoscope 2 and the axial direction of the reed of the reed switch 52 of the capsule endoscope 2 can accurately face the direction corresponding to the approaching position of the starter. For example, when the capsule endoscope 2 is rotated so that a long axis L242k of the mark image 286k of the T-shaped mark 242k is positioned within the reference area Sg in a state where an end of a short axis G242k of the mark image 286k of the T-shaped mark 242k faces a predetermined direction (a top-left direction in FIG. 24), it is possible to allow the step portions 142i2 of the inner casing 242 to appropriately abut on the area Sa or Sb of the capsule endoscope 2 and allow the axial direction of the reed of the reed switch 52 of the capsule endoscope 2 to accurately face the direction corresponding to the approaching position of the starter.

Thus, the operator rotates the jig 271 so that the long axis L242k of the mark image 286k of the T-shaped mark 242k is positioned within the reference area Sg in a state where the end of the short axis G242k of the mark image 286k of the T-shaped mark 242k faces the predetermined direction. Moreover, when the operator has checked on the display 286 that the long axis L242k of the mark image 286k of the T-shaped mark 242k is positioned within the reference area Sg in a state where the end of the short axis G242k of the T-shaped mark 242k faces the predetermined direction, since this is the case where the capsule endoscope 2 and the inner casing 242 are appropriately aligned, the operator operates the jig 271 to lift down the capsule endoscope 2 and inserts the capsule endoscope 2 into the hole 242e of the inner casing 242 from the longitudinal direction.

As described above, in the second embodiment, an index for alignment is provided on the inner casing 242, so that by using the index for alignment, it is possible to insert the capsule endoscope 2 into the inner casing 242 in a state where the step portions 142i2 of the inner casing 242 appropriately abut on the area Sa or Sb of the capsule endoscope 2, and the axial direction of the reed of the reed switch 52 of the capsule endoscope 2 accurately faces the direction corresponding to the approaching position of the starter.

In particular, in order to allow the step portions 142i2 of the inner casing 242 to abut on only the area Sa or Sb of the hemispheric dome portion 11a of the capsule endoscope 2 having a wide viewing angle and allow the axial direction of the reed of the reed switch 52 of the capsule endoscope 2 to accurately face the direction corresponding to the approaching position of the starter, a rotational error of approximately ±10° around the long axis of the capsule endoscope 2 is allowed. However, according to the second embodiment, by setting the reference area Sg to meet this error range and performing an operation of moving the capsule endoscope 2 so as to correspond to the reference area Sg, it is possible to realize accurate alignment within an allowable error range.

The image processor 283 may calculate a rotation amount around the long axis of the capsule endoscope 2 so that the mark image 286k of the T-shaped mark 242k is appropriately positioned within the reference area Sg based on the image of the T-shaped mark 242k and output sound information indicating the calculated rotation amount from the output unit 285. The operator can correctly align the inner casing 242 and the capsule endoscope 2 just by operating the jig 271 so that the capsule endoscope 2 rotates by the rotation amount corresponding to the sound information. Moreover, when the jig 271 is operated to rotate continuously, the image processor 283 may process respective items of image information transmitted sequentially from the capsule endoscope 2, determine whether the mark image 286k of the T-shaped mark 242k is appropriately positioned within the reference area Sg, and, when it is determined that the mark image 286k of the T-shaped mark 242k is appropriately positioned within the reference area Sg, output sound information or visual information such as light from the output unit 285 in order to inform the determination result. In this case, the operator can correctly align the inner casing 242 and the capsule endoscope 2 just by stopping the rotation operation on the jig 271 upon perceiving the sound information or the visual information such as light.

Moreover, in the second embodiment, although a case where the capsule endoscope 2 is moved to perform alignment has been described as an example, the alignment may be performed by moving the inner casing 242, and the alignment may be performed by moving both the capsule endoscope 2 and the inner casing 242.

Further, in the second embodiment, although an example in which the T-shaped mark 242k is used as an index for alignment has been described, the present invention is naturally not limited to this. The index for alignment may be a marker that is provided to a position where the short-axis end of the T-shaped mark 242k is positioned. The capsule endoscope 2 may be rotated around the long axis so that the marker falls within a predetermined reference area where the marker is to be positioned on an image of the marker captured by the capsule endoscope 2, and the alignment between the inner casing and the capsule endoscope 2 may be performed.

Further, the second embodiment is not limited to the capsule endoscope 2 having a wide viewing angle but can naturally be applied to a capsule endoscope in which only a portion corresponding to the hemispheric dome portion 11a is formed of a transparent material. In this case, the step portions 142i2 may abut on an optional area of the hemispheric dome portion 11a of the capsule endoscope as long as the area is outside the optical viewing angle. Since it is sufficient that the axial direction of the reed of the reed switch of the capsule endoscope approximately faces the direction corresponding to the approaching position of the starter, a rotational error of approximately 30° around the long axis of the capsule endoscope 2 is allowed.

Next, a third embodiment will be described. In the third embodiment, a case of automatically assembling a capsule endoscope kit that includes the inner casing and the capsule endoscope according to the second embodiment will be described.

Figure 25:
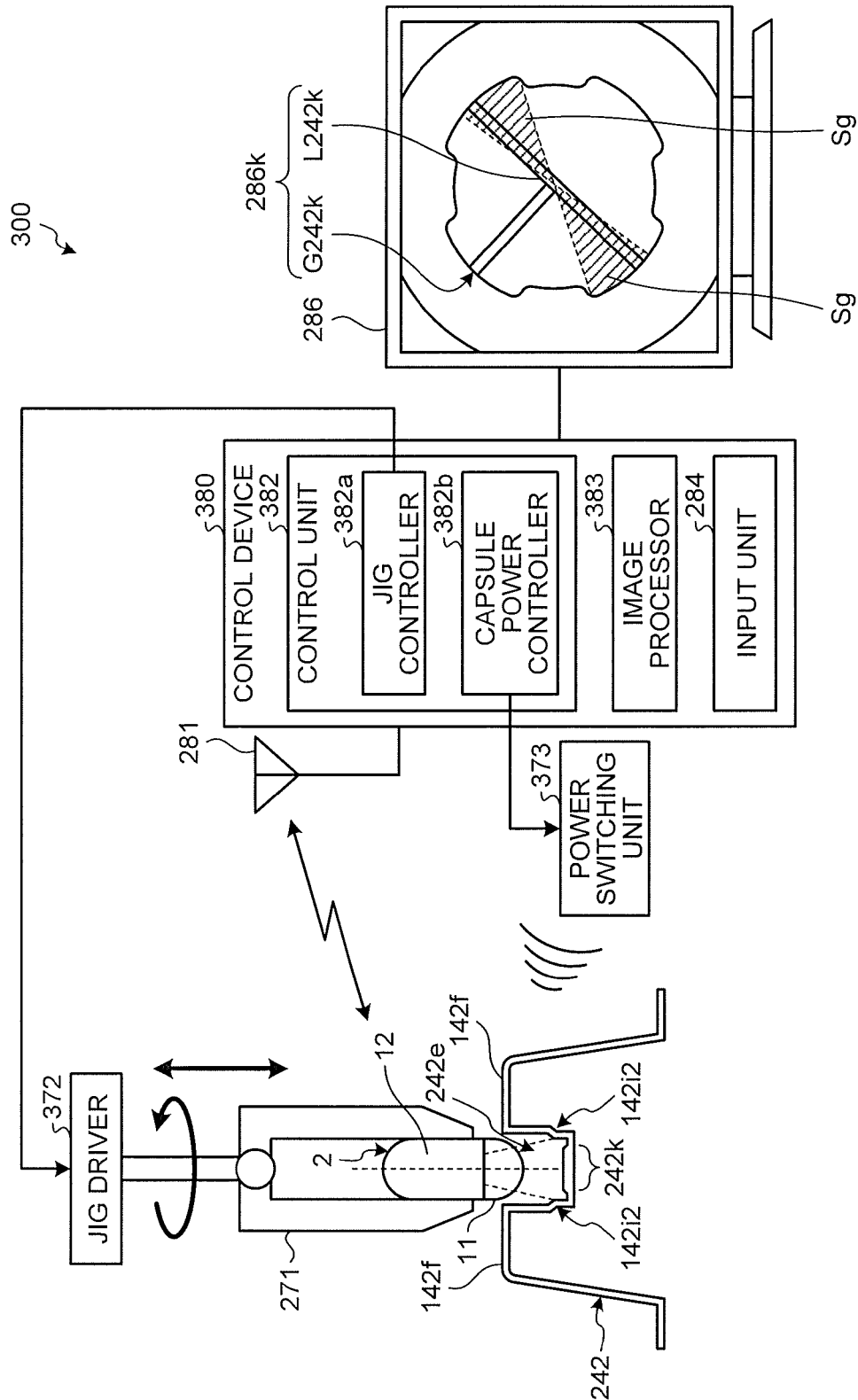
FIG. 25 is a schematic view illustrating a configuration of an assembly device of a capsule endoscope kit according to a third embodiment.

FIG. 25 is a schematic view illustrating a configuration of an assembly device of a capsule endoscope kit according to the third embodiment. As illustrated in FIG. 25, an assembly device 300 of a capsule endoscope kit according to the third embodiment includes the jig 271, a jig driver 372 that drives the jig 271, and a control device 380 that includes a power switching unit 373 that generates a magnetic field to switch on or off the power of the capsule endoscope 2.

The control device 380 further includes an antenna 281, a control unit 382 that controls each unit of the control device 380, an image processor 383 that processes the image information received by the antenna 281, an input unit 284, and a display 286.

The image processor 383 acquires the position of the T-shaped mark 242k based on the image information received by the antenna 281 and calculates a moving amount of at least one of the capsule endoscope 2 and the inner casing 242 so that the T-shaped mark 242k is positioned within the above-described reference area Sg in a predetermined direction. In the third embodiment, a case where the image processor 383 calculates the moving amount of the capsule endoscope 2 will be described as an example.

The control unit 382 includes a jig controller 382a that controls a driving operation of the jig driver 372 and a capsule power controller 382b that controls generation of the magnetic field by the power switching unit 373 to control the switching on or off of the power of the capsule endoscope 2.

Figure 26:
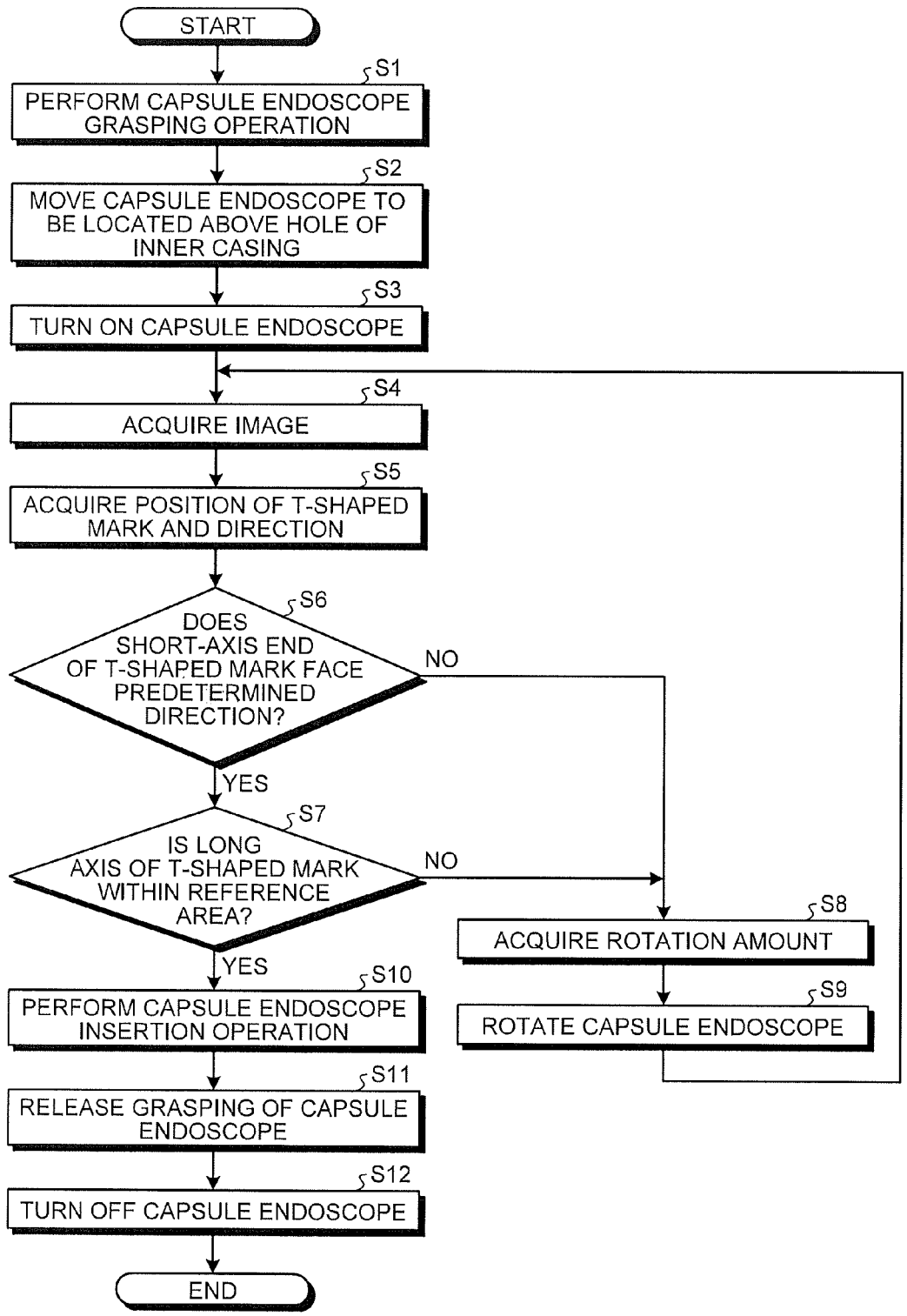
FIG. 26 is a flowchart illustrating a processing operation of the assembly device of the capsule endoscope kit illustrated in FIG. 25.

Next, a processing operation of the assembly device 300 of the capsule endoscope kit will be described. FIG. 26 is a flowchart illustrating the processing operation of the assembly device 300 of the capsule endoscope kit illustrated in FIG. 25.

As illustrated in FIG. 26, the jig controller 382a performs a capsule endoscope grasping operation of driving the jig driver 372 to cause the jig 271 to grasp the casing portion 12 which is the body portion of the capsule endoscope 2 (step S1). Subsequently, the jig controller 382a drives the jig driver 372 to cause the jig 271 to move the capsule endoscope 2 to be positioned above the hole 242e so that an end in the longitudinal direction of the capsule endoscope 2 closer to the imaging direction, that is, an end of the dome portion 11 faces the hole 242e of the inner casing 242 (step S2).

The capsule power controller 382b allows the power switching unit 373 to generate a predetermined magnetic field to turn on the power of the capsule endoscope 2 (step S3). As a result, the capsule endoscope 2 captures the image of the T-shaped mark 242k formed on the bottom surface of the hole 242e and wirelessly transmits information including the captured image information.

After that, in the control device 380, the antenna 281 receives the wireless information from the capsule endoscope 2 to acquire the images captured by the capsule endoscope 2 (step S4). The image processor 383 processes the image information received by the antenna 281 to acquire the position of the long axis L242 of the T-shaped mark 242k and the direction of the short-axis end G242k based on the mark image 286k of the T-shaped mark 242k (step S5). Subsequently, the image processor 383 determines whether the short-axis end G242k of the mark image 286k faces a predetermined direction (the top-left direction in FIG. 25) (step S6). When it is determined that the short-axis end G242k of the mark image 286k faces the predetermined direction (the top-left direction in FIG. 25) (Yes in step S6), the image processor 383 determines whether the long axis of the mark image 286k is positioned within the reference area Sg (step S7).

When it is determined that the short-axis end G242k of the mark image 286k does not face the predetermined direction (No in step S6), or when it is determined that the long axis of the mark image 286k is not positioned within the reference area Sg (No in step S7), the image processor 383 compares the position of the mark image 286k and the position of the reference area Sg to acquire a rotation amount of the capsule endoscope 2 for allowing the long axis L242 of the mark image 286k to be positioned in the reference area Sg in a state where the short-axis end G242k of the mark image 286k faces the predetermined direction (step S8).

Subsequently, the jig controller 382a controls the jig driver 372 so that the jig 271 rotates the capsule endoscope 2 by the rotation amount acquired by the image processor 383. As a result, the jig 271 rotates the capsule endoscope 2 by the rotation amount acquired by the image processor 383 (step S9). Moreover, returning to step S4, the antenna 281 receives the image information transmitted from the capsule endoscope 2 and acquires the images captured by the capsule endoscope 2 after the capsule endoscope 2 is rotated.

On the other hand, when the image processor 383 determines that the long axis of the mark image 286k is positioned within the reference area Sg (Yes in step S7), since the alignment between the inner casing 242 and the capsule endoscope 2 is realized, the jig controller 382a performs a capsule endoscope insertion operation of driving the jig driver 372 to lift down the jig 271 until the hemispheric dome portion 11a of the capsule endoscope 2 abuts on the step portions 142i2 and inserting the capsule endoscope 2 into the hole 242e of the inner casing 242 from the longitudinal direction (step S10). After that, the jig controller 382a drives the jig driver 372 to release the grasping of the capsule endoscope 2 by the jig 271 (step S11). Subsequently, the capsule power controller 382b turns off the power of the capsule endoscope 2 by causing the power switching unit 373 to stop generating the magnetic field (step S12). The step (step S12) of turning off the power of the capsule endoscope 2 may be performed before the capsule endoscope insertion operation (step S10) is performed or before the grasping of the capsule endoscope 2 is released (step S11) after the image processor 383 determines that the long axis of the mark image 286k is positioned within the reference area Sg (Yes in step S7). In this way, consumption of the battery of the capsule endoscope 2 may be decreased. After that, the assembly device 300 fits the inner casing 242 that holds the capsule endoscope 2 into the outer casing 141, sterilizes the inside of the outer casing 141, and blocks the opening of the outer casing 141 with the sterilizing sheet 143. In this way, the assembling of the capsule endoscope kit ends.

As described above, in the third embodiment, by processing the image of the T-shaped mark 242k captured by the capsule endoscope 2 to calculate the moving amount of the capsule endoscope 2 and moving the capsule endoscope 2, it is possible to automatically assemble the capsule endoscope kit in which the capsule endoscope 2 is held in a state where the step portions 142i2 of the inner casing 242 appropriately abut on the area Sa or Sb of the capsule endoscope 2, and the axial direction of the reed of the reed switch 52 of the capsule endoscope 2 appropriately faces the direction corresponding to the approaching position of the starter.

In the third embodiment, although a case where the capsule endoscope 2 is moved to perform alignment has been described as an example, the alignment may be performed by moving the inner casing 242, and the alignment may be performed by moving both the capsule endoscope 2 and the inner casing 242.

Next, a fourth embodiment will be described. In the second and third embodiments, although a case where the T-shaped mark formed on the bottom surface of the inner casing is used as an index for alignment has been described, another example of the index for alignment will be described in the fourth embodiment.

Figure 27:
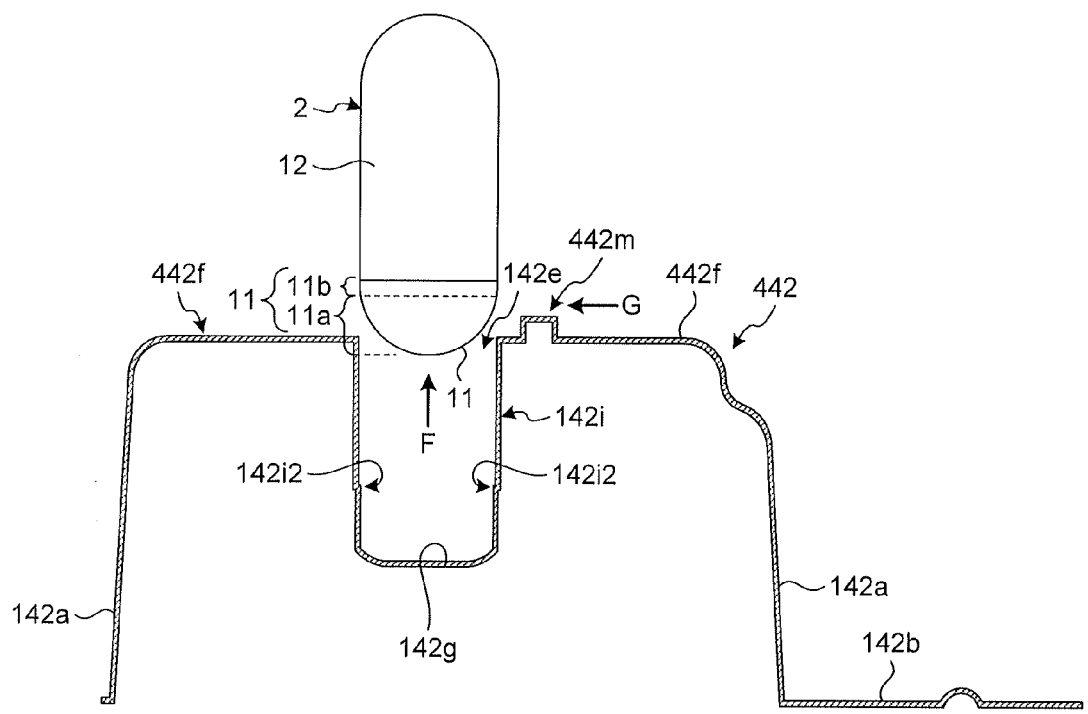
FIG. 27 is a cross-sectional view of an inner casing according to a fourth embodiment.

FIG. 27 is a cross-sectional view of an inner casing according to the fourth embodiment. FIG. 27 illustrates a case where the inner casing is cut along a cutting plane that passes through a principal side surface of a hole of the inner casing according to the fourth embodiment.

As illustrated in FIG. 27, an inner casing 442 according to the fourth embodiment has a configuration in which one projecting portion 442m that protrudes upward in the figure is formed on a base portion 442f as compared to the inner casing 142 described in the first embodiment. The projecting portion 442m functions as an index for alignment between the step portions 142i2 of the hole 142e and the above-described area Sa or Sb of the outer surface of the hemispheric dome portion 11a of the capsule endoscope 2, on which the step portions 142i2 abut.

Figure 28:
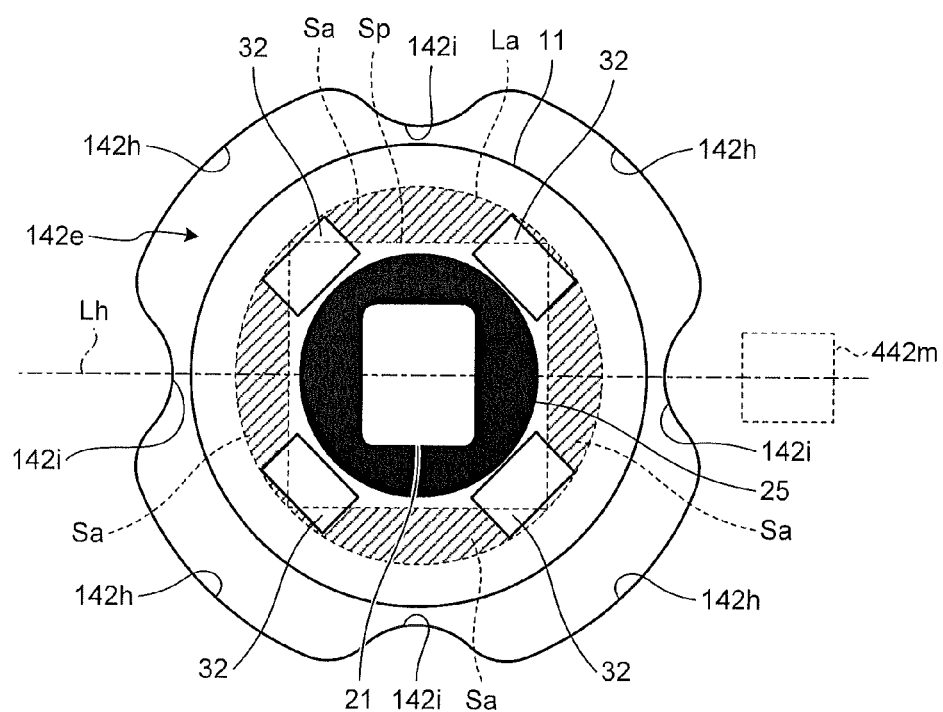
FIG. 28 is a view taken along an arrow F of FIG. 27.

As for the alignment between the capsule endoscope 2 and the inner casing 442, a case, on which the step portions 142i2 abut the area Sa of the dome portion 11 will be described as an example. FIG. 28 is a view taken along an arrow F of FIG. 27. In FIG. 28, a curve La represents a curve that corresponds to the optical viewing angle boundary of the capsule endoscope 2, and an area Sp represents a passing area of the light entering the imaging element 42. In FIG. 28, the area Sa is also illustrated.

As illustrated in FIG. 28, when the capsule endoscope 2 and the projecting portion 442m are seen from a direction that extends from the bottom surface 142g of the hole 142e to the opening of the hole 142e, four LEDs 32 are provided at an equal interval on a circumference that passes the diagonal line of the area Sp. Four step portions 142i2 are formed at an equal interval on a circumference about the central axis of the hole 142e. The projecting portion 442m is formed on a straight line Lh that connects the ends of two facing protruding portions 142i. The width of the projecting portion 442m in the vertical direction of the figure is shorter than the distance between adjacent two LEDs 32.

In order to allow the step portions 142i2 on the surface of the protruding portions 142i of the hole 142e to abut on the area Sa of the hemispheric dome portion 11a, the direction of the capsule endoscope 2 or the inner casing 442 may be adjusted so that the projecting portion 442m of the inner casing 442 is positioned between the adjacent LEDs 32 when the capsule endoscope 2 and the projecting portion 442m are seen from a direction that extends from the bottom surface 142g of the hole 142e to the opening of the hole 142e.

Since this capsule endoscope 2 uses the dome portion 11 in which a portion of the cylindrical portion is transparent as a casing, the LEDs 32 and the lens holding frame 25 can be viewed through the transparent dome portion 11 with the naked eyes when the capsule endoscope 2 is seen from the lateral direction. Moreover, since the LEDs 32 are often formed of a member which appears white when seen from the side surface, the lens holding frame 25 is generally formed so as to appear black in order to prevent reflection of light. Thus, the operator can distinguish the LEDs 32 and the lens holding frame 25 with the naked eyes. Moreover, the inner casing 442 is formed of a resin material that becomes semi-transparent when the material is heated during molding. Thus, the operator can distinguish the projecting portion 442m and the lens holding frame 25 with the naked eyes.

Therefore, the operator may adjust the direction of the capsule endoscope 2 or the inner casing 442 so that the projecting portion 442m of the inner casing 442 is positioned between the adjacent LEDs 32 while seeing the capsule endoscope 2 from the lateral direction. In other words, the operator may adjust the direction of the capsule endoscope 2 or the inner casing 442 so that the projecting portion 442m faces a position between adjacent two LEDs 32. Further, it is possible to perform alignment of both more accurately by adjusting the direction of the capsule endoscope 2 or the inner casing 442 so that both sides of the lens holding frame 25 visible between the LEDs 32 and the projecting portion 442m have the same width. Accurate alignment with the naked eyes can be realized by using the contrast difference between the white LEDs 32, the milky white projecting portion 442m, and the black lens holding frame 25.

Figure 29:
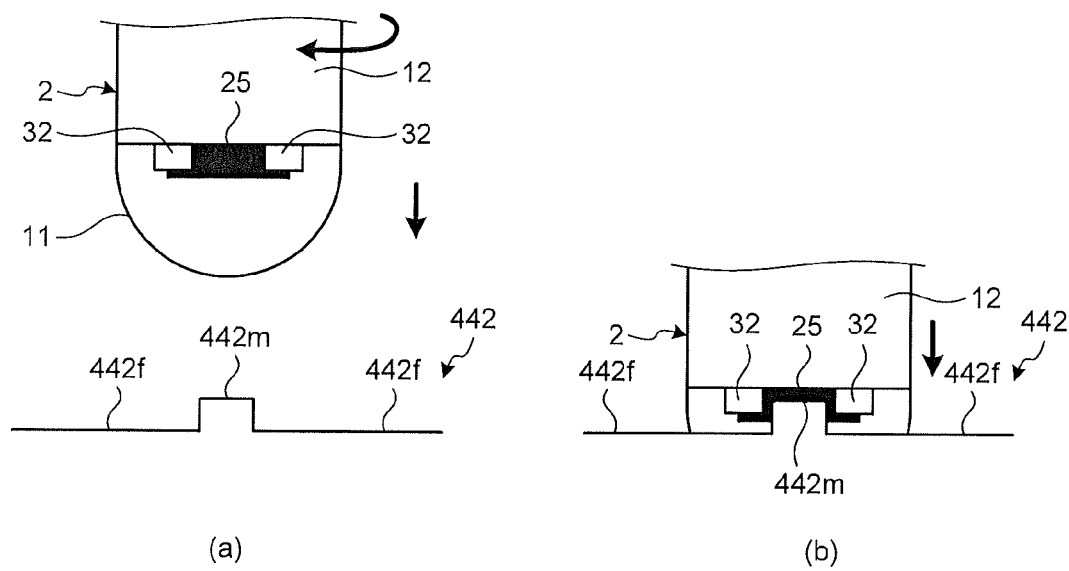
FIG. 29 is a view taken along an arrow G of FIG. 27.

FIG. 29 is a schematic view illustrating the alignment between the capsule endoscope 2 and the inner casing 442 according to the fourth embodiment and is a view taken along an arrow G of FIG. 27. The operator grasps the casing portion 12 which is the body portion of the capsule endoscope 2 using the jig 271 to move the capsule endoscope 2 to be positioned above the hole 142e so that as illustrated in FIG. 29(a), an end in the longitudinal direction of the capsule endoscope 2 closer to the imaging direction, that is an end of the dome portion 11 faces the hole 142e of the inner casing 442. In this case, the operator sees the inner casing 442 and the capsule endoscope 2 from the lateral direction of the capsule endoscope 2 so that as illustrated in FIG. 29(a), the projecting portion 442m of the inner casing 442 and the LEDs 32 of the capsule endoscope 2 are within the view of the operator. Subsequently, the operator operates the jig 271 to slowly lift down the capsule endoscope 2. Concurrently, the operator rotates the capsule endoscope 2 around the long axis so that the projecting portion 442m of the inner casing 442 is positioned between adjacent two LEDs 32. Moreover, after rotating the capsule endoscope 2 until the projecting portion 442m is positioned between the adjacent two LEDs 32 as illustrated in FIG. 29(b), the operator operates the jig 271 to lift down the capsule endoscope 2 until the step portions 142i2 abut on the hemispheric dome portion 11a and inserts the capsule endoscope 2 into the hole 242e of the inner casing 442 from the longitudinal direction.

As described above, in the fourth embodiment, one projecting portion 442m is provided on an extension line of the protruding portions 142i of the base portion 442f as an index for alignment. In the fourth embodiment, it is possible to store the capsule endoscope 2 in the inner casing 442 so that the step portions 142i2 appropriately abut on the area Sa of the capsule endoscope 2 by moving at least one of the capsule endoscope 2 and the inner casing 442 so that the projecting portion 442m faces the position between the adjacent two LEDs 32 of the LEDs 32 that form an illumination system of the capsule endoscope 2. Since the above-described area Sb is larger than the area Sa, by aligning the capsule endoscope 2 and the inner casing 442 in the same manner, it is possible to allow the step portions 142i2 to appropriately abut on the area Sa of the capsule endoscope 2.

Further, in the fourth embodiment, one marker 12n (see FIG. 30) may be provided at a position corresponding to the axial direction of the reed of the reed switch 52 inside the capsule endoscope 2 as the reference position in the circumferential direction of the capsule endoscope, and the position of the projecting portion 442m of the inner casing 442 may be set to the position corresponding to the approaching position of the starter. By inserting the capsule endoscope 2 into the hole 142e while aligning the marker 12n and the projecting portion 442m, it is possible to allow the step portions 142i2 to appropriately abut on the area Sa or Sb of the outer surface of the hemispheric dome portion 11a of the capsule endoscope 2 and to allow the starter to accurately approach the axial direction of the reed of the reed switch 52 of the capsule endoscope 2.

Figure 30:
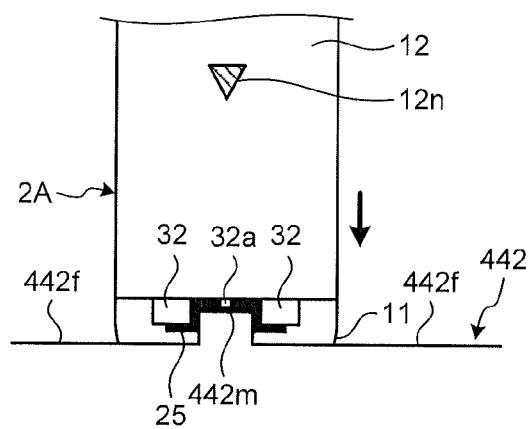
FIG. 30 is a schematic view illustrating alignment between another capsule endoscope and the inner casing according to the fourth embodiment.

Moreover, as in the case of a capsule endoscope 2A of FIG. 30, a projecting portion 32a may be provided at a position between the respective LEDs 32 corresponding to the axial direction of the reed of the reed switch 52 inside the capsule endoscope 2 as an index for alignment that has the same function as the marker 12n. In this case, by inserting the capsule endoscope 2 into the hole 142e while aligning the projecting portion 32a of the capsule endoscope 2A and the projecting portion 442m of the inner casing 442, it is possible to allow the step portions 142i2 to appropriately abut on the area Sa or Sb of the hemispheric dome portion 11a of the capsule endoscope 2 and to allow the starter to accurately approach the axial direction of the reed of the reed switch 52 of the capsule endoscope 2A.

Figure 31:
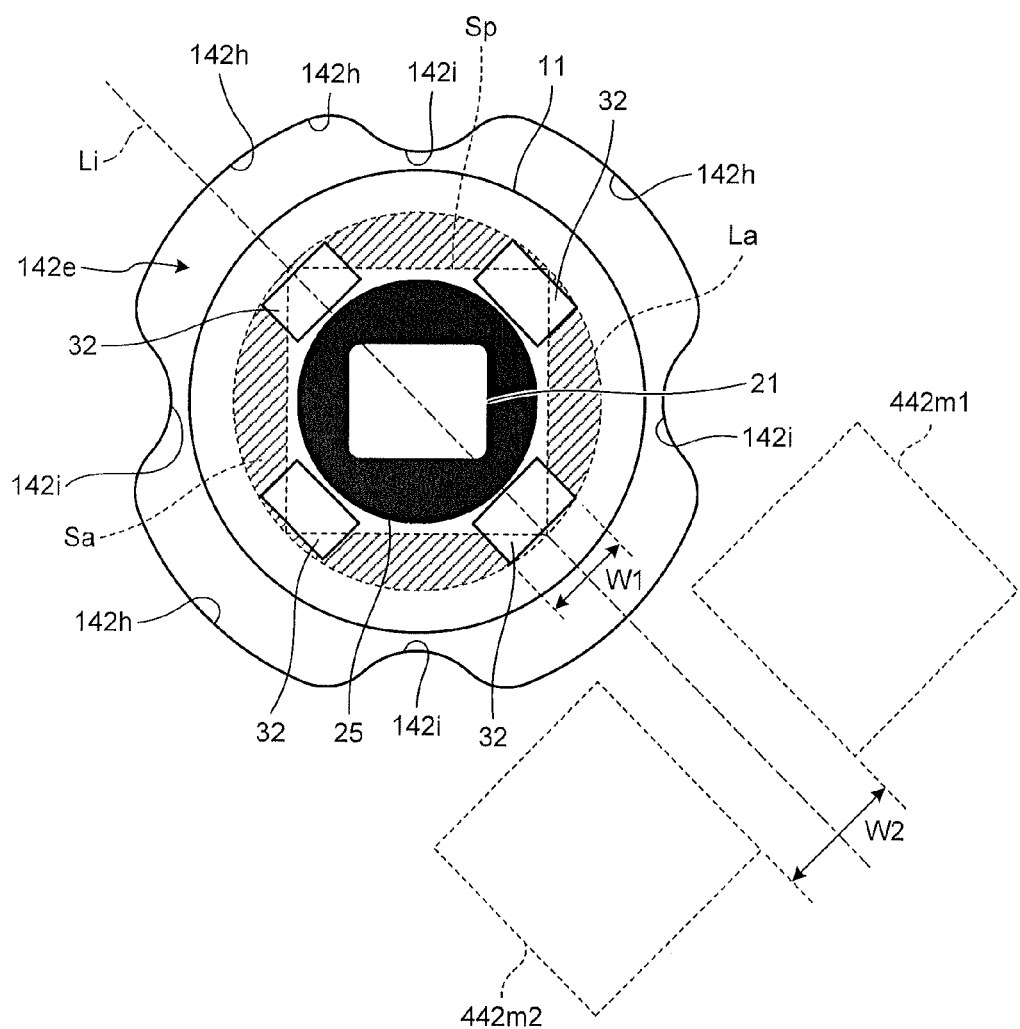
FIG. 31 is a diagram illustrating another inner casing according to the fourth embodiment.
Figure 32:
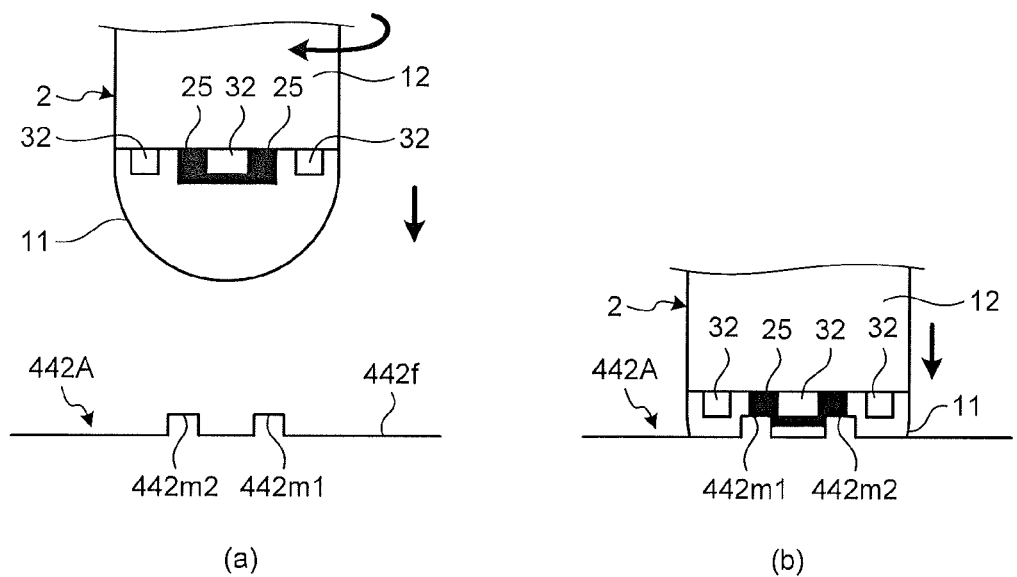
FIG. 32 is a schematic view illustrating alignment between a capsule endoscope and the inner casing illustrated in FIG. 31.

Moreover, the number of alignment projecting portions provided in the inner casing is not limited to one but may be two. FIG. 31 is a view illustrating another inner casing according to the fourth embodiment and corresponds to a view taken along the arrow F when the capsule endoscope 2 and the inner casing are positioned as illustrated in FIG. 27. FIG. 32 is a schematic view illustrating alignment between the capsule endoscope 2 and the inner casing illustrated in FIG. 31 and corresponds to a view taken along the arrow G when the capsule endoscope 2 and the inner casing are positioned as illustrated in FIG. 27.

In the case of an inner casing 442A illustrated in FIGS. 31 and 32, two projecting portions 442m1 and 442m2 are formed on a base portion 442f so that a straight line Li that connects the centers of two facing principal side surfaces 142h is at the boundary thereof. Moreover, a gap W2 between the two projecting portions 442m1 and 442m2 is set to be slightly larger than a width W1 of the outer surface of the LED 32.

Therefore, in order to allow the step portions 142i2 on the surface of the protruding portions 142i of the hole 142e to abut on the area Sa of the outer surface of the hemispheric dome portion 11a as illustrated in FIG. 31, the direction of the capsule endoscope 2 or the inner casing 442A may be adjusted so that the LEDs 32 of the capsule endoscope 2 are positioned between the two projecting portions 442m1 and 442m2 when the capsule endoscope 2 and the two projecting portions 442m1 and 442m2 are seen from a direction that extends from the bottom surface 142g of the hole 142e to the opening of the hole 142e. Further, it is possible to perform alignment of both more accurately by adjusting the direction of the capsule endoscope 2 or the inner casing 442 so that both sides of the lens holding frame 25 visible between the LEDs 32 and the projecting portion 442m have the same width.

Specifically, the operator grasps the body portion of the capsule endoscope 2 using the jig and sees the inner casing 442A and the capsule endoscope 2 from the lateral direction of the capsule endoscope 2 so that the two projecting portions 442m1 and 442m2 and any one of the LEDs 32 of the capsule endoscope 2 are within the view of the operator as illustrated in FIG. 32(a). Subsequently, after rotating the capsule endoscope 2 until the LED 32 is positioned between the two projecting portions 442m1 and 442m2 as illustrated in FIG. 32(b), the operator operates the jig 271 to lift down the capsule endoscope 2 until the step portions 142i2 abut on the hemispheric dome portion 11a and inserts the capsule endoscope 2 into the hole 142e of the inner casing 442A from the longitudinal direction.

Figure 33:
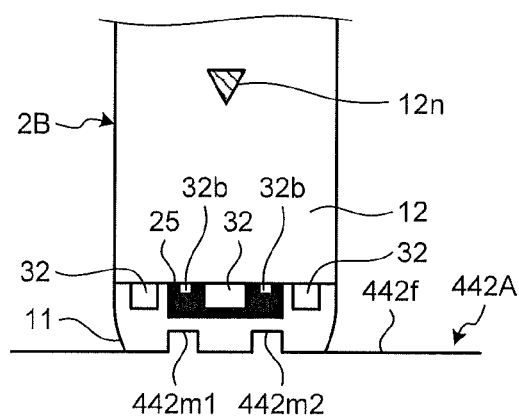
FIG. 33 is a schematic view illustrating alignment between another capsule endoscope and the inner casing illustrated in FIG. 31.

Further, similarly to the fourth embodiment, as in the case of a capsule endoscope 2B of FIG. 33, one marker 12n may be provided at a position corresponding to the axial direction of the reed of the reed switch 52 inside the capsule endoscope 2, and the positions of the two projecting portions 442m1 and 442m2 of the inner casing 442A may be set to the position corresponding to the approaching position of the starter as the predetermined position in the circumferential direction of the hole 142e of the inner casing 442A. By inserting the capsule endoscope 2 into the hole 142e while aligning the marker 12n so as to be positioned between the two projecting portions 442m1 and 442m2, it is possible to allow the step portions 142i2 to appropriately abut on the area Sa or Sb of the outer surface of the hemispheric dome portion 11a of the capsule endoscope 2 and to allow the starter to accurately approach the axial direction of the reed of the reed switch 52 of the capsule endoscope 2.

Moreover, as in the case of the capsule endoscope 2B, two projecting portions 32b may be provided on both sides of a reference LED 32 among the LEDs 32 corresponding to the axial direction of the reed of the reed switch 52 inside the capsule endoscope 2 as an index for alignment that has the same function as the marker 12n. In this case, by inserting the capsule endoscope 2 into the hole 142e while aligning the LED 32 interposed between the two projecting portions 32b of the capsule endoscope 2B with respect to the two projecting portions 442m1 and 442m2 of the inner casing 442A, it is possible to allow the step portions 142i2 to appropriately abut on the area Sa or Sb of the outer surface of the hemispheric dome portion 11a of the capsule endoscope 2 and to allow the starter to accurately approach the axial direction of the reed of the reed switch 52 of the capsule endoscope 2B.

Figure 34:
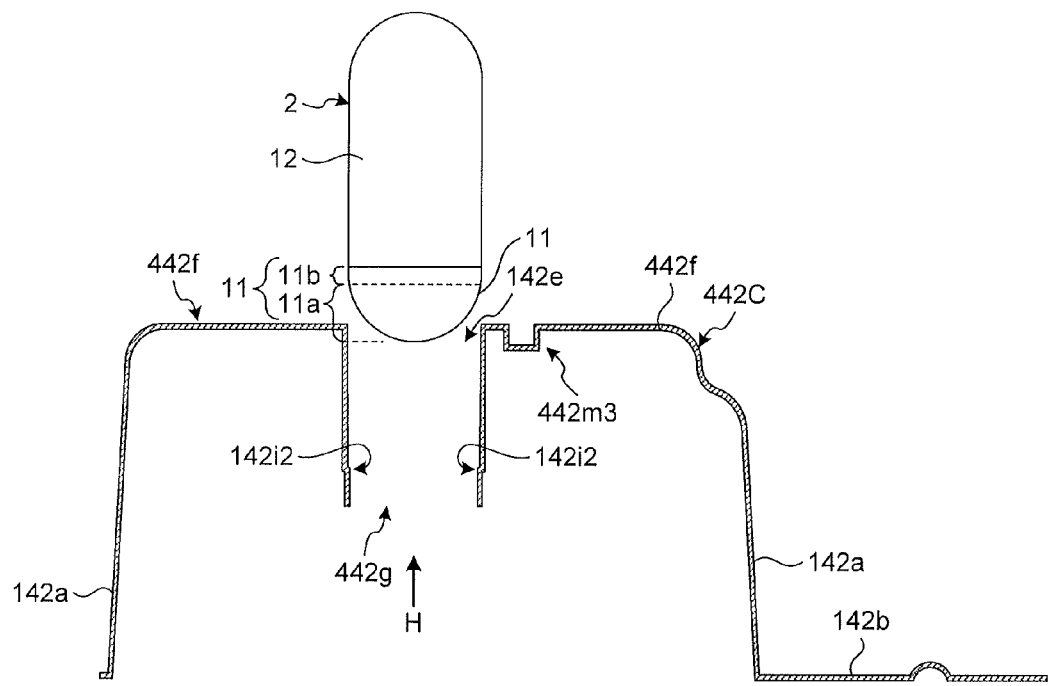
FIG. 34 is a cross-sectional view of an inner casing according to a second modification of the fourth embodiment.

FIG. 34 is a cross-sectional view of an inner casing according to a second modification of the fourth embodiment. FIG.

Figure 35:
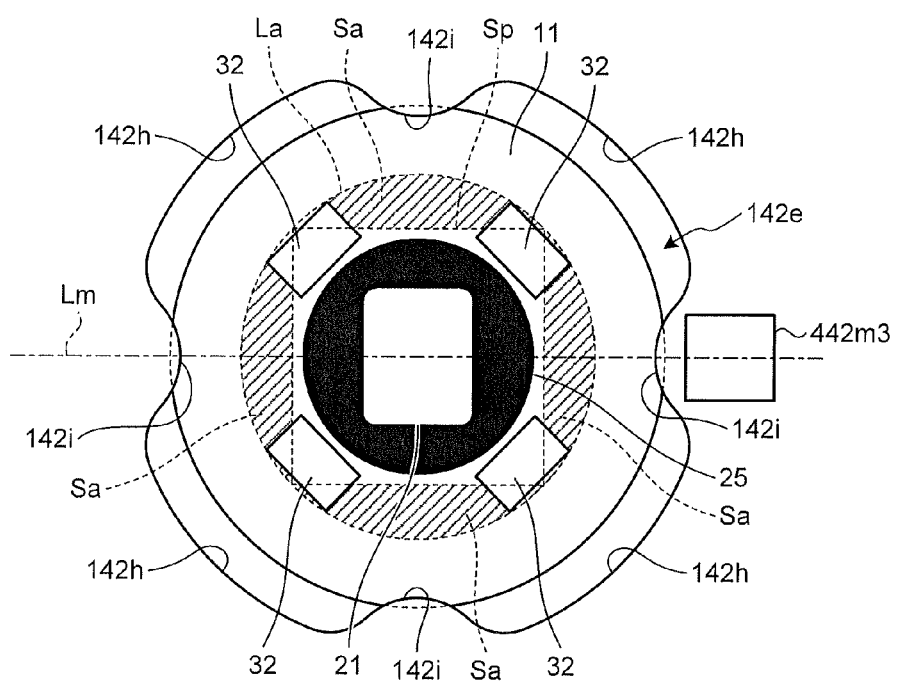
FIG. 35 is a view taken along an arrow H of FIG. 34.

34 illustrates a case where the inner casing is cut along a cutting plane that passes through a principal side surface of a hole of the inner casing according to the second modification of the fourth embodiment. FIG. 35 is a view taken along an arrow H of FIG. 34.

As illustrated in FIGS. 34 and 35, an inner casing 442C according to the second modification of the fourth embodiment has a configuration in which one projecting portion 442m3 that protrudes downward in the figure is provided on the base portion 442f at the same position as the projecting portion 442m as compared to the inner casing 442 according to the fourth embodiment. Further, the bottom surface of the hole 142e is opened. A bottom surface-side opening 442g of the hole 142e is set so as to be located on the lower side in the figure than the step portions 142i2.

In order to allow the step portions 142i2 on the surface of the protruding portions 142i of the hole 142e to abut on the area Sa as illustrated in FIG. 35, the direction of the capsule endoscope 2 or the inner casing 442C may be adjusted so that the projecting portion 442m3 of the inner casing 442C is positioned between the adjacent LEDs 32 when the capsule endoscope 2 and the projecting portion 442m are seen from a direction that extends from the opening 442g of the hole 142e to the opening of the hole 142e.

In this case, since the bottom surface portion of the hole 142e is opened, the operator grasps the body portion of the capsule endoscope 2 using the jig 271 and sees the inner casing 442C from the side of the opening 442g of the hole 142e so that the projecting portion 442m3 and any two adjacent LEDs 32 of the capsule endoscope 2 are within the view of the operator. Subsequently, after rotating the capsule endoscope 2 until the projecting portion 442m3 of the inner casing 442 is positioned between the adjacent two LEDs 32 as illustrated in FIG. 34, the operator operates the jig 271 to insert the capsule endoscope 2 into the hole 142e of the inner casing 442C from the longitudinal direction until the step portions 142i2 abut on the hemispheric dome portion 11a.

Moreover, a marker may be provided on the illumination substrate 31 so as to correspond to the axial direction of the reed of the reed switch 52 inside the capsule endoscope 2, and the position of the projecting portion 442m3 of the inner casing 442C may be set to the position corresponding to the approaching position of the starter. By inserting the capsule endoscope 2 into the hole 142e while aligning the marker of the illumination substrate 31 and the projecting portion 442m3, it is possible to allow the step portions 142i2 to appropriately abut on the area Sa or Sb of the outer surface of the hemispheric dome portion 11a of the capsule endoscope 2 and to allow the starter to accurately approach the axial direction of the reed of the reed switch 52 of the capsule endoscope 2.

Figure 36:
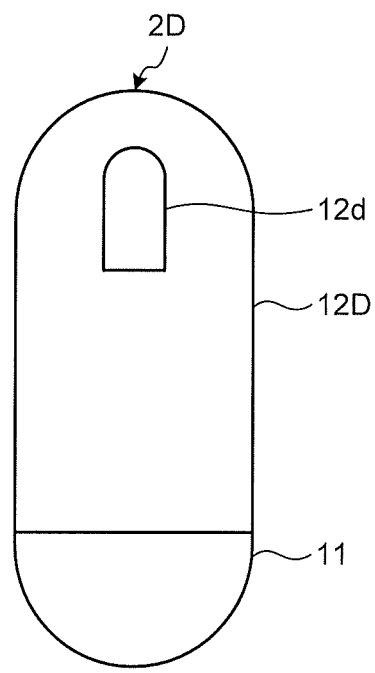
FIG. 36 is a front view of a capsule endoscope according to a third modification of the fourth embodiment.
Figure 37:
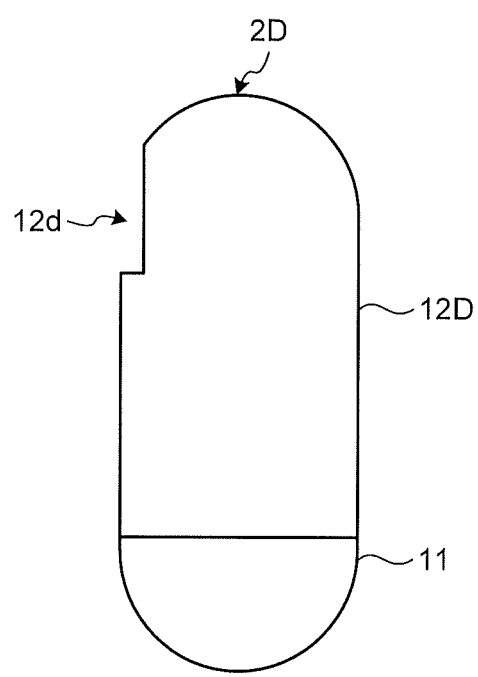
FIG. 37 is a side view of the capsule endoscope according to the third modification of the fourth embodiment.

FIG. 36 is a front view of a capsule endoscope according to a third modification of the fourth embodiment. FIG. 37 is a side view of the capsule endoscope according to the third modification of the fourth embodiment. As illustrated in FIGS. 36 and 37, in a capsule endoscope 2D of the third modification of the fourth embodiment, a D-shaped portion 12d is provided on a casing portion 12D which is a body portion.

Figure 38:
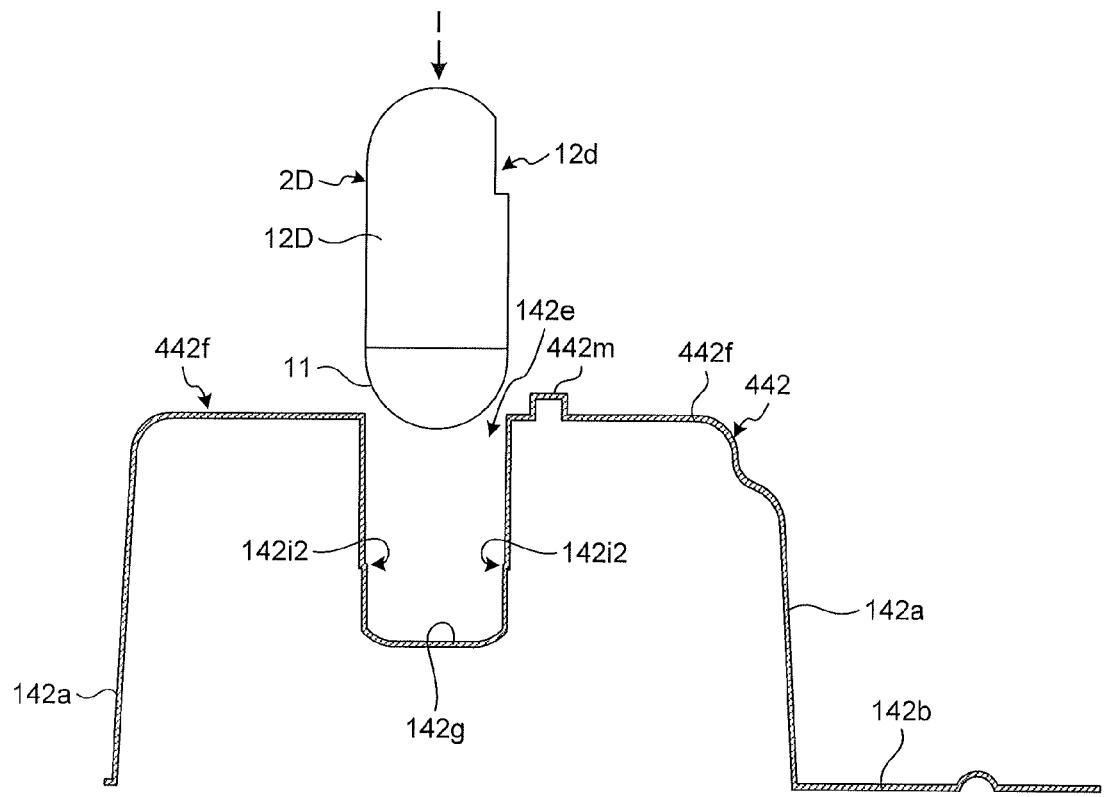
FIG. 38 is a diagram illustrating alignment between the capsule endoscope illustrated in FIGS. 36 and 37 and the inner casing illustrated in FIG. 27.
Figure 39:
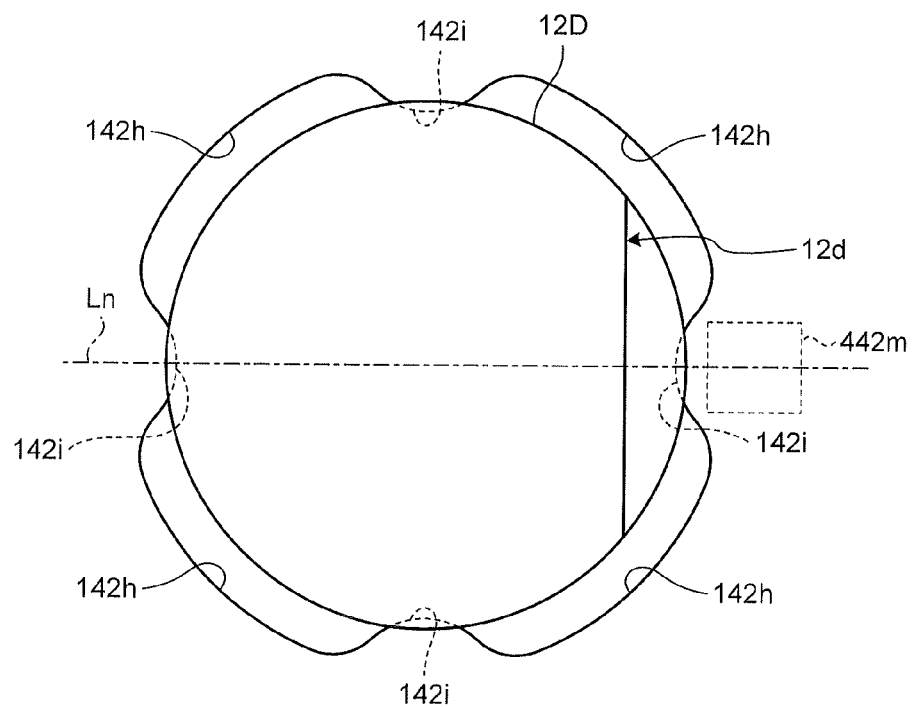
FIG. 39 is a view taken along an arrow I of FIG. 38.

Next, alignment between the capsule endoscope 2D and the inner casing 442 will be described with reference to FIGS. 38 and 39. FIG. 38 is a view illustrating the alignment between the capsule endoscope 2D and the inner casing 442. FIG. 38 schematically illustrates the capsule endoscope 2D together with a cross-sectional shape of the inner casing 442. FIG. 39 is a view taken along an arrow I of FIG. 38.

Here, the D-shaped portion 12d of the capsule endoscope 2D is formed at a position corresponding to the axial direction of the reed of the reed switch 52 inside the capsule endoscope 2D. The D-shaped portion is a portion obtained by notching a portion of an outer circumferential surface of the capsule endoscope 2D to form a flat surface. Moreover, the position of the D-shaped portion 12d is set such that the step portions 142i2 abut on the area Sa or Sb of the outer surface of the above-described hemispheric dome portion 11a when the D-shaped portion 12d faces the step portions 142i2 of the inner casing 442.

Thus, in order to allow the step portions 142i2 on the surface of the protruding portions 142i of the hole 142e illustrated in FIG. 38 to abut the area Sa or Sb, the direction of the capsule endoscope 2D or the inner casing 442 may be adjusted so that the projecting portion 442m faces the D-shaped portion 12d of the capsule endoscope 2D as illustrated in FIG. 39 when the capsule endoscope 2D and the inner casing 442 are seen from above.

Specifically, the operator grasps the body portion of the capsule endoscope 2 using the jig 271 and sees the inner casing 442 and the capsule endoscope 2D from the longitudinal direction of the capsule endoscope 2 so that the projecting portion 442m and the D-shaped portion 12d of the capsule endoscope 2D are within the view of the operator. Subsequently, after rotating the capsule endoscope 2D until the projecting portion 442m faces the D-shaped portion 12d as illustrated in FIG. 39, the operator operates the jig 271 to lift down the capsule endoscope 2D and inserts the capsule endoscope 2D into the hole 142e of the inner casing 442 from the longitudinal direction.

The position of the projecting portion 442m of the inner casing 442 may be set to the position corresponding to the approaching position of the starter. In this case, by inserting the capsule endoscope 2D into the hole 142e while aligning the projecting portion 442m so as to face the D-shaped portion 12d, it is possible to allow the step portions 142i2 to appropriately abut on the area Sa or Sb of the outer surface of the hemispheric dome portion 11a of the capsule endoscope 2 and to allow the starter to accurately approach the axial direction of the reed of the reed switch 52 of the capsule endoscope 2D.

Further, when two D-shaped portions 12d are provided so as to face with the long axis of the capsule endoscope 2 interposed, a marker may be provided to the D-shaped portion 12d that faces the projecting portion 442m so that the two D-shaped portions can be distinguished.

Next, a fifth embodiment will be described. In the fifth embodiment, a case of automatically assembling a capsule endoscope kit that includes an inner casing and a capsule endoscope will be described using the inner casing according to the fourth embodiment. As the fifth embodiment, a case of storing the inner casing 442 according to the fourth embodiment in the capsule endoscope 2 will be described as an example.

Figure 40:
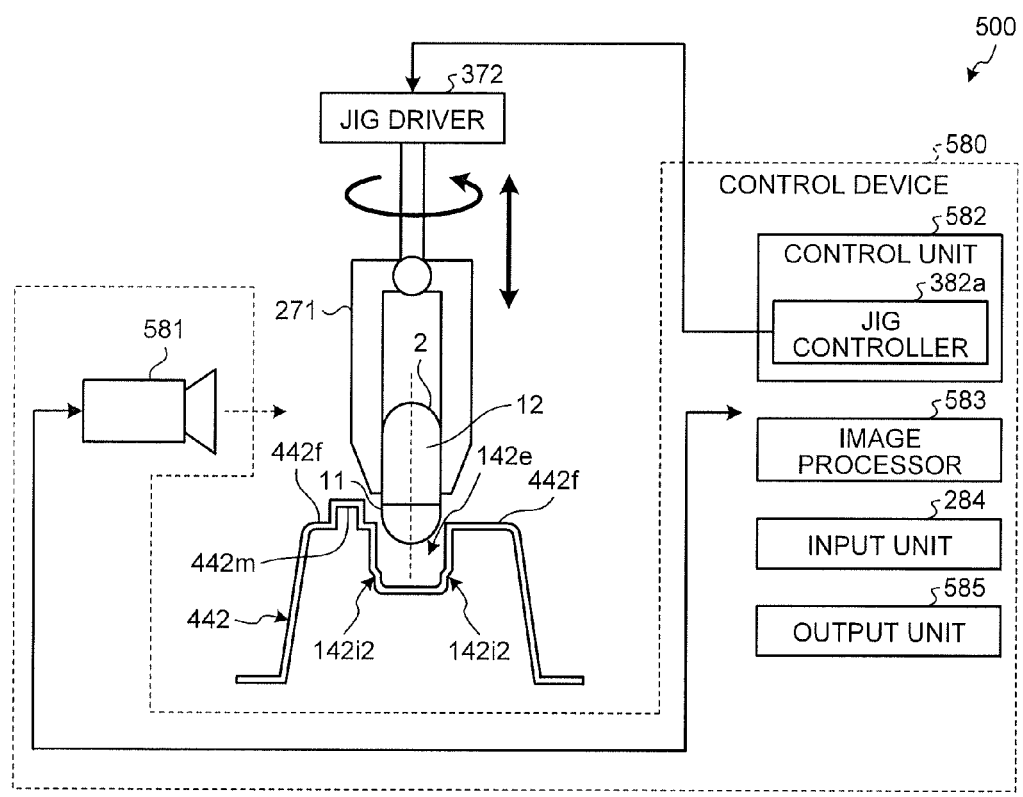
FIG. 40 is a schematic view illustrating a configuration of an assembly device of a capsule endoscope kit according to a fifth embodiment.

FIG. 40 is a schematic view illustrating a configuration of an assembly device of a capsule endoscope kit according to the fifth embodiment. As illustrated in FIG. 40, an assembly device 500 of a capsule endoscope kit according to the fifth embodiment includes a jig 271, a jig driver 372 that drives the jig 271, and a control device 580.

The control device 580 includes an imaging unit 581 that captures the image of the adjacent two LEDs 32 of the capsule endoscope 2 and the projecting portion 442m of the inner casing 442 from the lateral direction of the capsule endoscope 2, a control unit 582 that includes a jig controller 382a and controls each unit of the control device 580, an image processor 583 that processes the image captured by the imaging unit 581, and an input unit 284. The control device 580 may further include an output unit 585 that outputs at least one of visual information and sound information.

The image processor 583 acquires the position of two adjacent LEDs 32 in the capsule endoscope 2 and the position of the projecting portion 442*m* of the inner casing 442 based on the image captured by the imaging unit 581 and calculates the moving amount of at least one of the capsule endoscope 2 and the inner casing 442 so that the projecting portion 442*m* is positioned between the two adjacent LEDs 32 on the image. In the fifth embodiment, a case where the image processor 583 calculates the moving amount of the capsule endoscope 2 will be described as an example.

Figure 41:
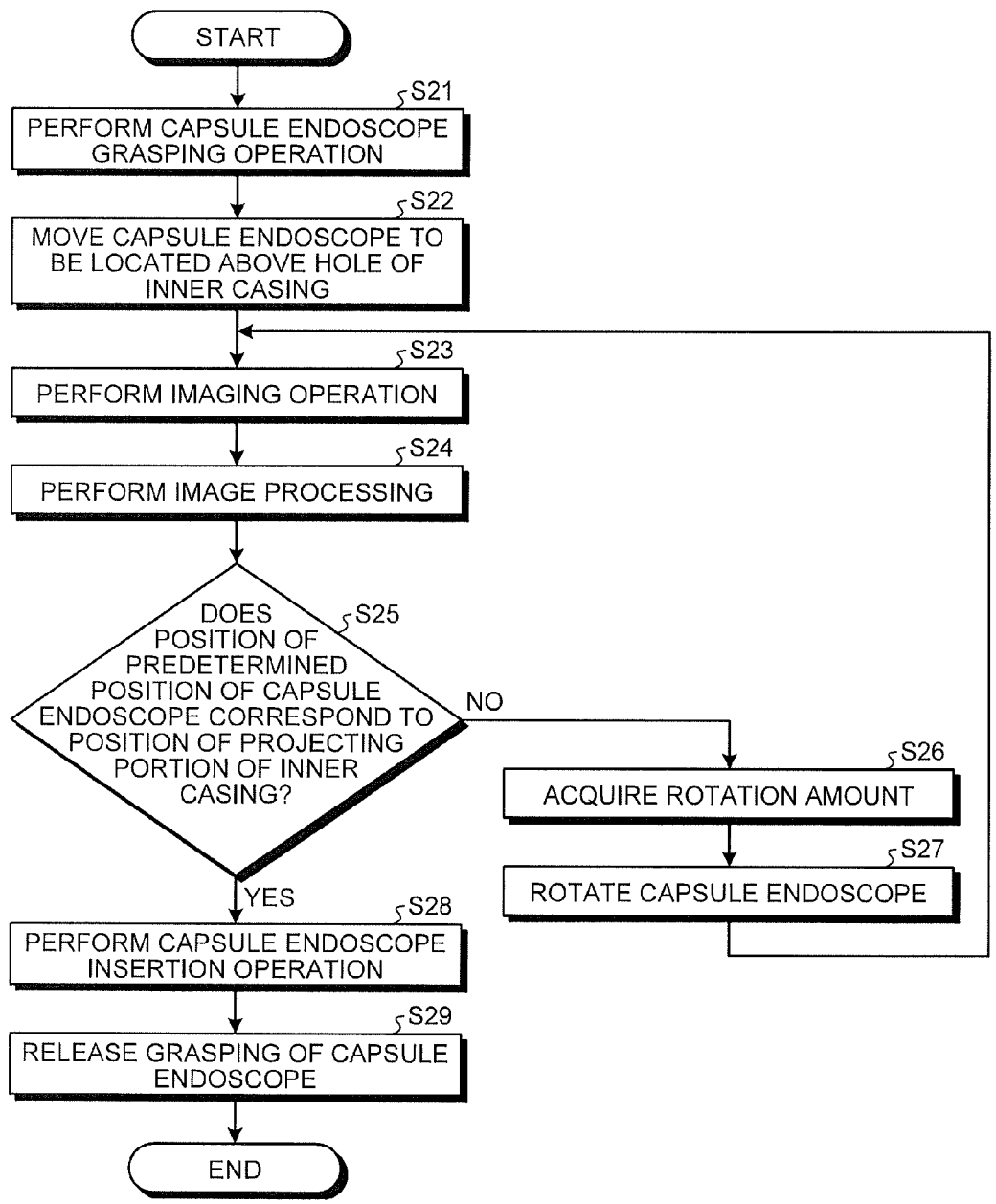
FIG. 41 is a flowchart illustrating a processing operation of the assembly device of the capsule endoscope kit illustrated in FIG. 40.

Next, a processing operation of the assembly device 500 of the capsule endoscope kit will be described. FIG. 41 is a flowchart illustrating the processing operation of the assembly device 500 of the capsule endoscope kit illustrated in FIG. 40.

As illustrated in FIG. 41, the jig controller 382*a* performs a capsule endoscope grasping operation of driving the jig driver 372 to cause the jig 271 to grasp the casing portion 12D which is a body portion of the capsule endoscope 2 (step S21). Subsequently, the jig controller 382*a* drives the jig driver 372 to cause the jig 271 to move the capsule endoscope 2 to be positioned above the hole 142*e* so that an end in the longitudinal direction of the capsule endoscope 2 closer to the imaging direction, that is, an end of the dome portion 11 faces the hole 142*e* of the inner casing 442 (step S22).

After that, the imaging unit 581 performs an imaging operation of capturing the image of the two adjacent LEDs 32 of the capsule endoscope 2 and the projecting portion 442*m* of the inner casing 442 from the lateral direction of the capsule endoscope 2 (step S23). Subsequently, in the control device 580, the image processor 583 processes the image captured by the imaging unit 581 (step S24), and acquires the positions of the two adjacent LEDs 32 of the capsule endoscope 2 and the position of the projecting portion 442*m* of the inner casing 442. For example, the image processor 583 acquires the positions of the adjacent two LEDs 32 of the capsule endoscope 2 and the position of the projecting portion 442*m* of the inner casing 442 by comparing the contrasts between the two LEDs 32 and the projecting portion 442*m* and the lens holding frame 25 appearing on the background of the LEDs 32 and the projecting portion 442*m* on the image captured by the imaging unit 581.

Subsequently, the image processor 583 determines whether the position of a predetermined portion of the capsule endoscope 2 corresponds to the position of the inner casing 442 (step S25). Specifically, the image processor 583 determines whether the projecting portion 442*m* is positioned between the two adjacent LEDs 32 on the image.

When the image processor 583 determines that the position of a predetermined portion of the capsule endoscope 2 does not correspond to the position of the inner casing 442 (No in step S25), that is when the image processor 583 determines that the projecting portion 442*m* is not positioned between the two adjacent LEDs 32 on the image, the image processor 583 compares the positions of the two adjacent LEDs 32 and the position of the projecting portion 442*m* of the inner casing 442 to acquire a rotation amount of the capsule endoscope 2 for allowing the projecting portion 442*m* to be positioned between the two adjacent LEDs 32 on the image (step S26).

Subsequently, the jig controller 382*a* controls the jig driver 372 so that the jig 271 rotates the capsule endoscope 2 by the rotation amount acquired by the image processor 583. As a result, the jig 271 rotates the capsule endoscope 2 by the rotation amount acquired by the image processor 583 (step S27). Moreover, returning to step S23, the antenna 281 captures the image of the two adjacent LEDs 32 and the projecting portion 442*m* from the lateral direction of the capsule endoscope 2.

On the other hand, when the image processor 583 determines that the position of the predetermined portion of the capsule endoscope 2 corresponds to the position of the inner casing 442 (Yes in step S25), that is when the image processor 583 determines that the projecting portion 442*m* is positioned between the two adjacent LEDs 32 on the image, since the alignment between the inner casing 442 and the capsule endoscope 2 is realized, the jig controller 382*a* performs a capsule endoscope insertion operation of driving the jig driver 372 to lift down the jig 271 until the step portions 142*i*2 abut on the hemispheric dome portion 11*a* and inserting the capsule endoscope 2 into the hole 142*e* of the inner casing 442 from the longitudinal direction (step S28). After that, the jig controller 382*a* drives the jig driver 372 to release the grasping of the capsule endoscope 2 by the jig 271 (step S29). After that, the assembly device 300 fits the inner casing 442 that holds the capsule endoscope 2 into the outer casing 141, sterilizes the inside of the outer casing 141, and blocks the opening of the outer casing 141 with the sterilizing sheet 143. In this way, the assembling of the capsule endoscope kit ends.

As described above, in the fifth embodiment, by processing the image of the LEDs 32 and the projecting portion 442*m* captured by the imaging unit 581 to calculate the moving amount of the capsule endoscope 2 and moving the capsule endoscope 2, it is possible to automatically assemble the capsule endoscope kit in which the step portions 142*i*2 of the inner casing 442 appropriately abut on the area Sa or Sb of the capsule endoscope 2.

Further, when assembling a capsule endoscope kit that stores the capsule endoscope 2A in which the projecting portion 32*a* described in the fourth embodiment is provided, by processing the image of the two LEDs 32 having the projecting portion 32*a* interposed therebetween and the projecting portion 442*m* and calculating the rotation amount of the capsule endoscope 2A so that the projecting portion 442*m* is positioned between the LEDs 32 having the projecting portion 32*a* interposed therebetween, it is possible to automatically assemble the capsule endoscope kit in which the capsule endoscope 2A is held in a state where the axial direction of the reed of the reed switch 52 of the capsule endoscope 2A appropriately faces the direction corresponding to the approaching position of the starter.

In a first modification of the fifth embodiment, an assembly device of a capsule endoscope kit that includes the inner casing 442A according to the first modification of the fourth embodiment as an inner casing will be described.

In this case, in the assembly device 500, after the operations of steps S21 and S22 illustrated in FIG. 41 are performed, in step S23, the imaging unit 581 captures the image of the two projecting portions 442*m*1 and 442*m*2 and the LED 32 from the lateral direction of the capsule endoscope 2. Subsequently, in step S24, the image processor 583 processes the image captured by the imaging unit 581 to acquire the positions of the two projecting portions 442*m*1 and 442*m*2 and the position of the LED 32 of the capsule endoscope 2. Subsequently, in step S25, the image processor 583 determines whether the LED 32 of the capsule endoscope 2 is positioned between the two projecting portions 442*m*1 and 442*m*2. When it is determined that the LED 32 is not positioned between the two projecting portions 442*m*1 and 442*m*2 (No in step S25), the image processor 583 compares the positions of the two projecting portions 442*m*1 and 442*m*2 and the position of the LED 32 to acquire the rotation amount of the capsule endoscope 2 for allowing the LED 32 to be positioned between the two projecting portions 442$m$1 and 442$m$2 on the image (step S26). Then, the jig 271 rotates the capsule endoscope 2 by the rotation amount (step S27), and then the flow returns to step S23.

On the other hand, when the image processor 583 determines that the LED 32 is positioned between the two projecting portions 442$m$1 and 442$m$2 (Yes in step S25), a capsule endoscope insertion operation (step S28) and a capsule endoscope releasing operation (step S29) are performed. Then, the inner casing 442A is fitted into the outer casing 141, and the opening of the outer casing 141 is blocked with the sterilizing sheet 143. In this way, the assembling of the capsule endoscope kit ends.

Further, when assembling a capsule endoscope kit that stores the capsule endoscope 2B in which two projecting portions 32$b$ described in the first modification of the fourth embodiment is provided, by processing the image of the LED 32 interposed between the two projecting portions 32$b$ and the projecting portions 442$m$1 and 442$m$2 and calculating the rotation amount of the capsule endoscope 2B for allowing the LED 32 interposed between the projecting portions 32$b$ to be positioned between the two protruding portions 442$m$1 and 442$m$2, it is possible to automatically assemble the capsule endoscope kit in which the capsule endoscope 2B is held in a state where the axial direction of the reed of the reed switch 52 of the capsule endoscope 2B accurately faces the direction corresponding to the approaching position of the starter.

In the first modification of the fifth embodiment, a case of using the inner casing 442C according to the second modification of the fourth embodiment as an inner casing will be described.

Figure 42:
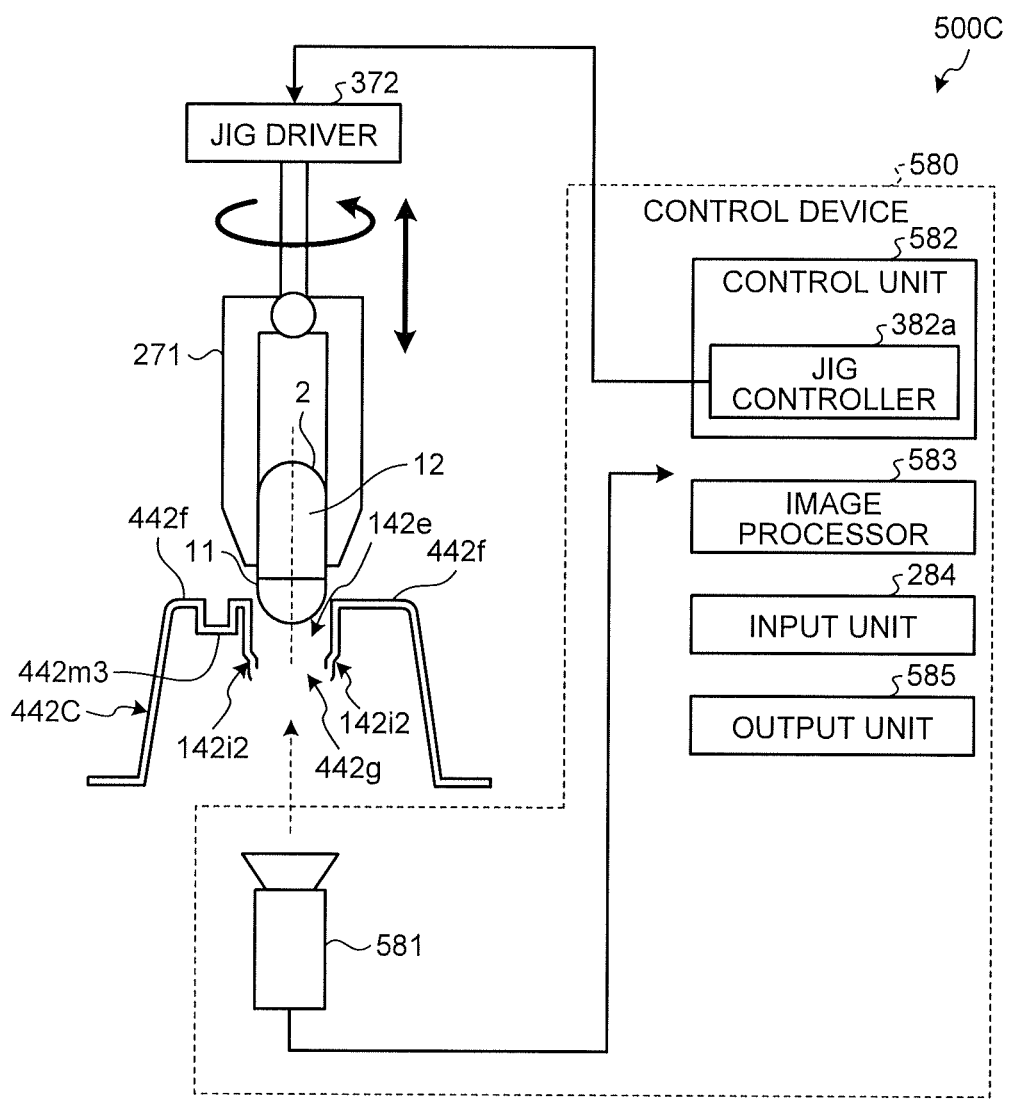
FIG. 42 is a schematic view illustrating a configuration of an assembly device of a capsule endoscope kit according to a second modification of the fifth embodiment.

FIG. 42 is a schematic view illustrating a configuration of an assembly device of a capsule endoscope kit according to a second modification of the fifth embodiment. As illustrated in FIG. 42, in an assembly device 500C of a capsule endoscope kit according to the second modification of the fifth embodiment, the imaging unit 581 captures the image of the projecting portion 442$m$3 and two LEDs 32 from the lower side of the bottom surface-side opening 442$g$ of the hole 142$e$ of the inner casing 442C.

In the assembly device 500C, after the operations of steps S21 and S22 illustrated in FIG. 41 are performed, in step S23, the imaging unit 581 captures the image of the projecting portion 442$m$3 and two LEDs 32 from the lower side of the bottom surface-side opening 442$g$ of the hole 142$e$ of the inner casing 442C. Subsequently, in step S24, the image processor 583 processes the image captured by the imaging unit 581 to acquire the positions of the adjacent two LEDs 32 and the position of the projecting portion 442$m$3 of the inner casing 442C. Subsequently, in step S25, the image processor 583 determines whether the projecting portion 442$m$3 is positioned between the two adjacent LEDs 32 on the image. When it is determined that the projecting portion 442$m$3 is not positioned between the two adjacent LEDs 32 (No in step S25), the image processor 583 compares the positions of the adjacent two LEDs 32 and the position of the projecting portion 442$m$3 to acquire the rotation amount of the capsule endoscope 2 for allowing the projecting portion 442$m$3 to be positioned between the two adjacent LEDs 32 on the image (step S26). Then, the jig 271 rotates the capsule endoscope 2 by the rotation amount (step S27) and then the flow returns to step S23.

On the other hand, when the image processor 583 determines that the projecting portion 442$m$3 is positioned between the two adjacent LEDs 32 (Yes in step S25), a capsule endoscope insertion operation (step S28) and a capsule endoscope releasing operation (step S29) are performed. Then, the inner casing 442C is fitted into the outer casing 141, and the opening of the outer casing 141 is blocked with the sterilizing sheet 143. In this way, the assembling of the capsule endoscope kit ends.

As described above, in the fifth embodiment and the first and second modifications of the fifth embodiment, the position of a predetermined position of an illumination system of the capsule endoscope 2, 2A, or 2B and the position of the projecting portion 442$m$, 442$m$1, 442$m$2, or 442$m$3 of the inner casing 442, 442A, or 442C may be acquired based on the image captured by the imaging unit 581, and at least one of the capsule endoscope 2, 2A, or 2B and the inner casing 442, 442A, or 442C may be moved so that the predetermined portion of the illumination system of the capsule endoscope 2, 2A, or 2B faces the projecting portion 442$m$, 442$m$1, 442$m$2, or 442$m$3 of the inner casing 442, 442A, or 442C.

Third Modification of Fifth Embodiment

Moreover, a case of assembling a capsule endoscope kit in which the capsule endoscope 2D according to the third modification of the fourth embodiment is stored in the inner casing 442 as an inner casing will be described.

Figure 43:
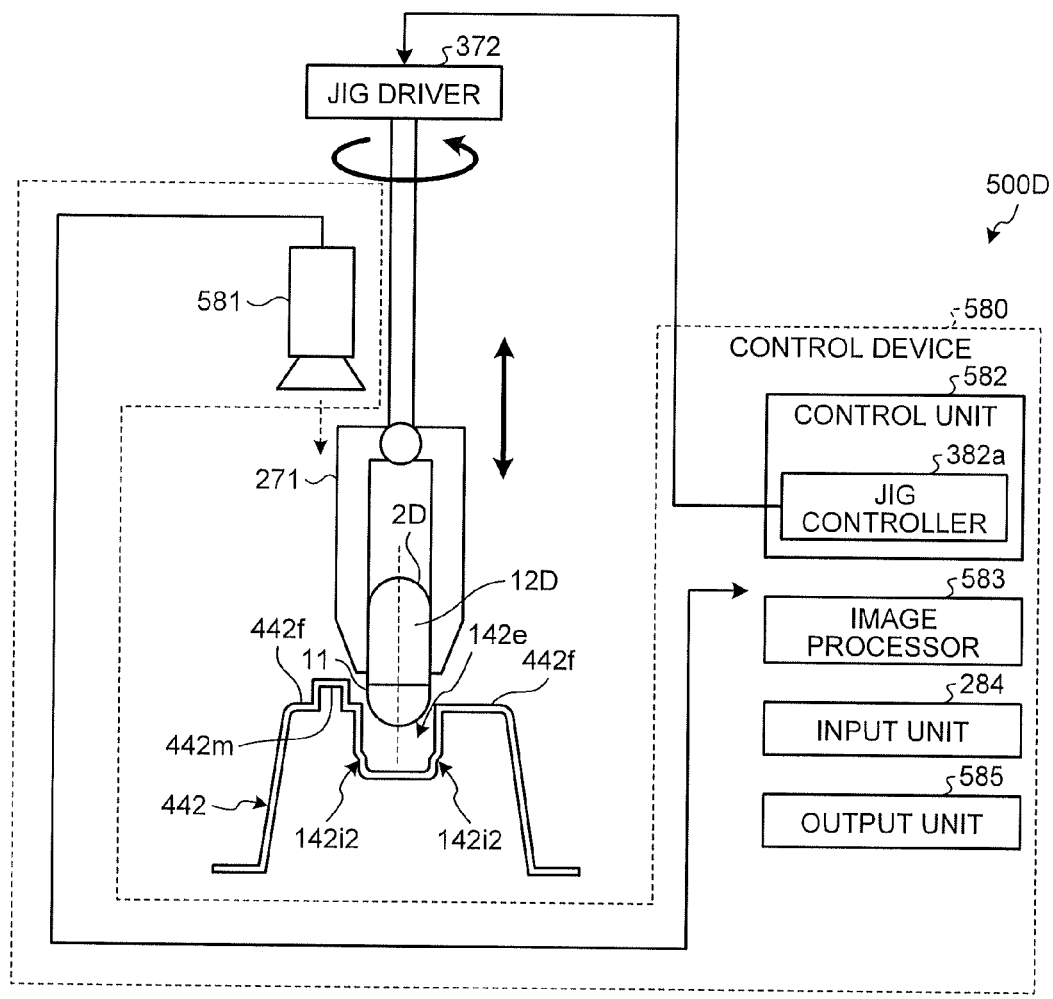
FIG. 43 is a schematic view illustrating a configuration of an assembly device of a capsule endoscope kit according to a third modification of the fifth embodiment.

FIG. 43 is a schematic view illustrating a configuration of an assembly device of a capsule endoscope kit according to a third modification of the fifth embodiment. As illustrated in FIG. 43, in an assembly device 500D of a capsule endoscope kit according to the third modification of the fifth embodiment, the imaging unit 581 captures the image of the projecting portion 442$m$ and the D-shaped portion 12$d$ of the capsule endoscope 2D from the upper side of the hole 142$e$ of the inner casing 442.

In this case, in the assembly device 500D, after the operations of steps S21 and S22 illustrated in FIG. 41 are performed, in step S23, the imaging unit 581 captures the image of the projecting portion 442$m$ and the D-shaped portion 12$d$ of the capsule endoscope 2D from the upper side of the hole 142$e$ of the inner casing 442. Subsequently, in step S24, the image processor 583 processes the image captured by the imaging unit 581 to acquire the position of the projecting portion 442$m$ and the position of the D-shaped portion 12$d$ of the capsule endoscope 2D. Subsequently, in step S25, the image processor 583 determines whether the projecting portion 442$m$ faces the D-shaped portion 12$d$ of the capsule endoscope 2D on the image. When it is determined that the projecting portion 442$m$ does not face the D-shaped portion 12$d$ of the capsule endoscope 2D (No in step S25), the image processor 583 compares the position of the projecting portion 442$m$ and the position of the D-shaped portion 12$d$ of the capsule endoscope 2D to acquire the rotation amount of the capsule endoscope 2 for allowing the projecting portion 442$m$ to face the D-shaped portion 12$d$ of the capsule endoscope 2D on the image (step S26). Then, the jig 271 rotates the capsule endoscope 2 by the rotation amount (step S27) and then the flow returns to step S23.

On the other hand, when the image processor 583 determines that the projecting portion 442$m$ faces the D-shaped portion 12$d$ of the capsule endoscope 2D (Yes in step S25), a capsule endoscope insertion operation (step S28) and a capsule endoscope grasping and releasing operation (step S29) are performed. Then, the inner casing 442 is fitted into the outer casing 141, and the opening of the outer casing 141 is blocked with the sterilizing sheet 143. In this way, the assembling of the capsule endoscope kit ends.

In this manner, the position of the D-shaped portion 12d of the capsule endoscope 2D and the position of the projecting portion 442m of the inner casing 442 may be acquired based on the image captured by the imaging unit 581, and at least one of the capsule endoscope D and the inner casing 442 may be moved so that the D-shaped portion 12d of the capsule endoscope 2D faces the projecting portion 442m of the inner casing 442.

As described above, the casing for storing the capsule endoscope, the capsule endoscope kit, the assembly method for assembling the capsule endoscope kit, and the assembly device for assembling the capsule endoscope kit according to the present invention are useful for a medical observation apparatus which is inserted into a human body to observe a subject area, and are particularly suitable for stably holding a capsule endoscope in a state where the function of capturing the subject is appropriately maintained.

Another advantages and modifications may easily occur to those skilled in the art. Thus, a broader aspect of the present invention is not limited to the specific details and representative embodiments illustrated and described above. Therefore, various changes can be made without departing from the spirit or scope of the general concept of the inventions defined by the attached claims and the equivalents thereof.

Moreover, the above embodiments are examples for practicing the present invention, and the present invention is not limited to these embodiments. Various modifications according to specifications or the like fall within the scope of the present invention. Further, it is obvious from the above descriptions that various different embodiments can occur within the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A casing for a capsule endo scope which includes a first casing that has a bottomed cylindrical shape and retains an imaging element therein and a transparent second casing that has a cylindrical portion and a hemispheric portion having the same outer diameter as an outer diameter of the first casing and engages with the first casing, in which at least an illumination system and a lens located on an outermost side are positioned inside the second casing, the casing comprising:
    a base portion having a planar shape;
    a holding portion provided at a center of the base portion so as to protrude in a direction orthogonal to a principal surface of the base portion and hold the capsule endoscope;
    a plurality of abutting portions each protruding from the holding portion and abutting on at least a portion of an outer surface of the hemispheric portion of the second casing, wherein each of the plurality of abutting portions is located inside an optical viewing angle of the capsule endoscope and does not contribute to generation and/or use of an image captured by the capsule endoscope to realize alignment in a longitudinal direction of the capsule endoscope; and
    an index for alignment of the abutting portions with respect to an area of the outer surface of the hemispheric portion of the second casing, on which the abutting portions abut.

2. The casing of the capsule endoscope according to claim 1, wherein the abutting portions abut on a portion of the outer surface of the hemispheric portion of the second casing, which is located inside the optical viewing angle of the capsule endoscope and is outside a passing area of light entering the imaging element.

3. The casing of the capsule endoscope according to claim 1, wherein the abutting portions abut on a portion of the outer surface of the hemispheric portion of the second casing, which is located inside the optical viewing angle of the capsule endoscope and corresponds to a portion that is not displayed when the image captured by the capsule endoscope is displayed on an image display device.

4. The casing of the capsule endoscope according to claim 1, wherein a plurality of the abutting portions are formed at positions which are located at an equal distance from a central axis of the holding portion and are line symmetrical to a predetermined straight line on a plane that is vertical to the central axis of the holding portion.

5. The casing of the capsule endoscope according to claim 1, wherein a plurality of the abutting portions are formed at an equal interval on a circumference about a central axis of the holding portion, which is located on a plane that is vertical to the central axis of the holding portion.

6. The casing of the capsule endoscope according to claim 1,
    wherein a portion of the holding portion other than the abutting portions has a diameter larger than the outer diameter of the first casing of the capsule endoscope, and
    a distal end of each of the abutting portions is positioned on a circle that has a diameter smaller than the outer diameter of the first casing of the capsule endoscope.

7. The casing of the capsule endoscope according to claim 1, wherein the index for alignment functions as an index for aligning a reference position in a circumferential direction of the capsule endoscope to a predetermined position in a circumferential direction of the holding portion of the casing.

8. The casing of the capsule endoscope according to claim 7,
    wherein the capsule endoscope includes a reed switch that performs a switching operation according to a change in a magnetic field according to an activation starter, and the capsule endoscope is turned on or off according to the switching operation of the reed switch, and
    the predetermined position in the circumferential direction of the holding portion is set to correspond to an approaching position of the starter with respect to the capsule endoscope that is stored in the casing.

9. The casing of the capsule endoscope according to claim 1, wherein the index for alignment is a T-shaped mark that is formed on a bottom surface of the holding portion.

10. The casing of the capsule endoscope according to claim 1, wherein the index for alignment is a projecting portion that is formed on the base portion.

11. A capsule endoscope kit comprising:
    a capsule endoscope including:
    a first casing that has a bottomed cylindrical shape and retains an imaging element therein;
    a transparent second casing that has a cylindrical portion and a hemispheric portion having the same outer diameter as an outer diameter of the first casing and engages with the first casing;
    an illumination system positioned inside the second casing; and
    a lens group in which at least an outermost lens is positioned inside the second casing;
    a casing for storing the capsule endoscope, including:

a base portion having a planar shape;

a holding portion provided at a center of the base portion so as to protrude in a direction orthogonal to a principal surface of the base portion and hold the capsule endoscope; and a plurality of abutting portions each protruding from the holding portion and abutting on at least a portion of an outer surface of the hemispheric portion of the second casing, wherein each of the plurality of abutting portions is located inside an optical viewing angle of the capsule endoscope and does not contribute to generation and/or use of an image captured by the capsule endoscope to realize alignment in a longitudinal direction of the capsule endoscope;

an outer casing that holds the casing for storing the capsule endoscope therein; and a sterilizing sheet that blocks the outer casing and has sterilizing gas permeability;

wherein the casing includes an index for alignment of the abutting portions with respect to an area of the outer surface of the hemispheric portion of the second casing, on which the abutting portions abut.

12. The capsule endoscope kit according to claim 11, wherein the abutting portions abut on a portion of the outer surface of the hemispheric portion of the second casing, which is located inside the optical viewing angle of the capsule endoscope and is outside a passing area of light entering the imaging element.

13. The capsule endoscope kit according to claim 11, wherein the abutting portions abut on a portion of the outer surface of the hemispheric portion of the second casing, which is located inside the optical viewing angle of the capsule endoscope and corresponds to a portion that is not displayed when the image captured by the capsule endoscope is displayed on an image display device.

14. The capsule endoscope kit according to claim 11, wherein a plurality of the abutting portions are formed at positions which are located at an equal distance from a central axis of the holding portion and are line symmetrical to a predetermined straight line on a plane that is vertical to the central axis of the holding portion.

15. The capsule endoscope kit according to claim 11, wherein a plurality of the abutting portions are formed at an equal interval on a circumference about a central axis of the holding portion, which is located on a plane that is vertical to the central axis of the holding portion.

16. The capsule endoscope kit according to claim 11, wherein a portion of the holding portion other than the abutting portions has a diameter larger than the outer diameter of the first casing of the capsule endoscope, and a distal end of each of the abutting portions is positioned on a circle that has a diameter smaller than the outer diameter of the first casing of the capsule endoscope.

17. The capsule endoscope kit according to claim 11, the index for alignment functions as an index for aligning a reference position in a circumferential direction of the capsule endoscope to a predetermined position in a circumferential direction of the holding portion of the casing.

18. The capsule endoscope kit according to claim 17, wherein the capsule endoscope includes a reed switch that performs a switching operation according to a change in a magnetic field according to an activation starter, and the capsule endoscope is turned on or off according to the switching operation of the reed switch, the reference position in the circumferential direction of the capsule endoscope is set to correspond to the axial direction of the reed switch, and the predetermined position in the circumferential direction of the holding portion is set to correspond to an approaching position of the starter with respect to the capsule endoscope that is stored in the casing.

19. The capsule endoscope kit according to claim 11, wherein the index for alignment is a T-shaped mark that is formed on a bottom surface of the holding portion.

20. The capsule endoscope kit according to claim 11, wherein the index for alignment is a projecting portion that is formed on the base portion.

21. An assembly method of a capsule endoscope kit which includes a capsule endoscope that has an imaging element and a wireless communication unit and a casing that includes a base portion in which a holding portion for storing the capsule endoscope is formed and an index for alignment that is formed on a bottom surface of the holding portion or the base portion so as to align a reference position in the circumferential direction of the capsule endoscope with respect to a predetermined position in the circumferential direction of the holding portion, the assembly method comprising:

grasping a body portion of the capsule endoscope and moving the capsule endoscope to be positioned above the holding portion so that an end in a longitudinal direction of the capsule endoscope closer to an imaging direction faces the holding portion; and aligning the reference position in the circumferential direction of the capsule endoscope with respect to the predetermined position in the circumferential direction of the holding portion by capturing an image of at least the index for alignment and inserting the capsule endoscope into the holding portion from the longitudinal direction.

22. The assembly method of the capsule endoscope kit according to claim 21, wherein the index for alignment is formed on the bottom surface of the holding portion, and the inserting of the capsule endoscope includes:

turning on the capsule endoscope;

acquiring the image of the index for alignment captured by the capsule endoscope;

acquiring a position of the index for alignment based on the image acquired in the acquiring of the image and moving at least one of the capsule endoscope and the casing so that the index for alignment is positioned within a reference area where the reference position in the circumferential direction of the capsule endoscope and the predetermined position in the circumferential direction of the holding portion maintain a predetermined positional relation;

inserting the capsule endoscope into the holding portion from the longitudinal direction; and turning off the capsule endoscope.

23. The assembly method of the capsule endoscope kit according to claim 21, wherein the index for alignment is a projecting portion that is formed on the base portion, the capsule endoscope includes a first casing having a bottomed cylindrical shape that forms the body portion and a transparent second casing which has a cylindrical portion and a hemispheric portion having the same outer diameter as an outer diameter of the first casing and engages with the first casing, and in which at least an illumination system, a lens located on an outermost side, and a portion of a lens holding frame that holds the lens therein are positioned inside the second casing, and the inserting of the capsule endoscope includes:

capturing an image of a predetermined portion of the capsule endoscope and the projecting portion;

acquiring a position of the predetermined portion of the capsule endoscope and a position of the projecting portion of the casing based on the image captured in the capturing of an image and moving at least one of the capsule endoscope and the casing so that the predetermined portion of the capsule endoscope and the projecting portion of the casing have a predetermined positional relation; and inserting the capsule endoscope into the holding portion from the longitudinal direction.

24. The assembly method of the capsule endoscope kit according to claim 23, wherein the capturing of an image involves capturing an image of a predetermined position of the illumination system of the capsule endoscope and the projecting portion, and the moving of at least one of the capsule endoscope and the casing involves acquiring the position of the predetermined portion of the illumination system of the capsule endoscope and the position of the projecting portion of the casing based on the image captured in the capturing of an image and moving at least one of the capsule endoscope and the casing so that the predetermined portion of the illumination system of the capsule endoscope faces the projecting portion of the casing.

25. The assembly method of the capsule endoscope kit according to claim 23, wherein the capsule endoscope includes a D-shaped portion on the body portion, the capturing of an image involves capturing an image of the D-shaped portion of the capsule endoscope and the projecting portion from an upper side of the capsule endoscope and the holding portion, and the moving of at least one of the capsule endoscope and the casing involves acquiring the position of the D-shaped portion of the capsule endoscope and the position of the projecting portion of the casing based on the image captured in the capturing of an image and moving at least one of the capsule endoscope and the casing so that the D-shaped portion of the capsule endoscope faces the projecting portion of the casing.

26. An assembly device of a capsule endoscope kit for assembling the capsule endoscope kit which includes a capsule endoscope that has an imaging element and a wireless communication unit and a casing that includes a base portion in which a holding portion for storing the capsule endoscope is formed and an index for alignment that is formed on a bottom surface of the holding portion or the base portion so as to align a reference position in the circumferential direction of the capsule endoscope with respect to a predetermined position in the circumferential direction of the holding portion, the assembly device comprising:

a grasping and moving unit for grasping a body portion of the capsule endoscope, lifting the grasped capsule endoscope about the longitudinal direction and lifting the capsule endoscope, and moving the capsule endoscope to be positioned above the holding portion so that an end in a longitudinal direction of the capsule endoscope closer to an imaging direction faces the holding portion; and a control unit for aligning the reference position in the circumferential direction of the capsule endoscope with respect to the predetermined position in the circumferential direction of the holding portion by capturing an image of at least the index for alignment and inserting the capsule endoscope into the holding portion from the longitudinal direction with respect to the grasping and moving unit.

27. The assembly device of the capsule endoscope kit according to claim 26, wherein the index for alignment is formed on the bottom surface of the holding portion, and the assembly device further includes a power switching unit capable of turning on or off the capsule endoscope, the control unit includes:

an image acquisition unit for acquiring the image of the index for alignment captured by the capsule endoscope;

an image processing unit for acquiring a position of the index for alignment based on the image acquired by the image acquisition unit and calculating a moving amount of at least one of the capsule endoscope and the casing so that the index for alignment is positioned within a reference area where the reference position in the circumferential direction of the capsule endoscope and the predetermined position in the circumferential direction of the holding portion maintain a predetermined positional relation; and a moving control unit for causing the grasping and moving unit to move at least one of the capsule endoscope and the casing by the moving amount calculated by the image processing unit and insert the capsule endoscope into the holding portion from a longitudinal direction, and the power switching unit turns on the capsule endoscope before the image acquisition unit acquires the image and turns off the capsule endoscope after the image processing unit acquires the moving amount.

28. The assembly device of the capsule endoscope kit according to claim 26, wherein the index for alignment is a projecting portion that is formed on the base portion, the capsule endoscope includes a first casing having a bottomed cylindrical shape that forms the body portion and a transparent second casing which has a cylindrical portion and a hemispheric portion having the same outer diameter as an outer diameter of the first casing and engages with the first casing, and in which at least an illumination system, a lens located on an outermost side, and a portion of a lens holding frame that holds the lens therein are positioned inside the second casing, and the control unit includes:

an imaging unit for capturing an image of a predetermined portion of the capsule endoscope and the projecting portion;

an image processing unit for acquiring a position of the predetermined portion of the capsule endoscope and a position of the projecting portion of the casing based on the image captured by the imaging unit and calculating a moving amount of at least one of the capsule endoscope and the casing so that the predetermined portion of the capsule endoscope and the projecting portion of the casing have a predetermined positional relation; and a moving control unit for causing the grasping and moving unit to move at least one of the capsule endoscope and the casing by the moving amount calculated by the image processing unit and to insert the capsule endoscope into the holding portion from a longitudinal direction.

* * * * *